United States Patent [19]

Ziemer et al.

[11] Patent Number: 5,698,539

[45] Date of Patent: Dec. 16, 1997

[54] MIXTURES OF HERBICIDES AND ANTIDOTES, (HETERO)-ARYLOXY COMPOUNDS, THEIR PREPARATION, COMPOSITIONS CONTAINING THEM, AND THEIR USE

[75] Inventors: Frank Ziemer, Kriftel/Ts; Lothar Willms, Hillscheid; Klaus Bauer, Hanau; Hermann Bieringer, Eppstein/Ts, all of Germany

[73] Assignee: Hoechst Aktiengesellschaft, Frankfurt, Germany

[21] Appl. No.: 461,443

[22] Filed: Jun. 5, 1995

Related U.S. Application Data

[63] Continuation of Ser. No. 68,416, May 27, 1993, abandoned.

[30] Foreign Application Priority Data

May 30, 1992 [DE] Germany .................... 42 17 928.9

[51] Int. Cl.[6] .................................... A01N 43/54
[52] U.S. Cl. ..................... 504/103; 504/105; 504/106; 504/110; 504/112; 544/316
[58] Field of Search ................... 504/53, 55, 88, 504/96, 223, 238, 103, 105, 106, 110, 112

[56] References Cited

U.S. PATENT DOCUMENTS

| H670 | 9/1989 | Kimura et al. ........................ 71/92 |
| 4,414,020 | 11/1983 | Heier et al. ........................ 71/108 |
| 4,668,276 | 5/1987 | Handte et al. ........................ 71/88 |

FOREIGN PATENT DOCUMENTS

| 1259200 | 9/1989 | Canada . |
| 0031938 | 7/1981 | European Pat. Off. . |
| 0088066 | 9/1983 | European Pat. Off. . |
| 0112799 | 7/1984 | European Pat. Off. . |
| 0154153 | 9/1985 | European Pat. Off. . |
| 0170906 | 2/1986 | European Pat. Off. . |
| 0223606 | 5/1987 | European Pat. Off. . |
| 0249708 | 12/1987 | European Pat. Off. . |
| 0269707 | 12/1987 | European Pat. Off. . |
| 0287072 | 10/1988 | European Pat. Off. . |
| 0287079 | 10/1988 | European Pat. Off. . |
| 0293062 | 11/1988 | European Pat. Off. . |
| 0321846 | 6/1989 | European Pat. Off. . |
| 0335409 | 10/1989 | European Pat. Off. . |
| 0363040 | 4/1990 | European Pat. Off. . |
| 0426476 | 5/1991 | European Pat. Off. . |
| 0435186 | 7/1991 | European Pat. Off. . |
| WO 91/13065 | of 0000 | WIPO . |

*Primary Examiner*—Matthew V. Grumbling
*Attorney, Agent, or Firm*—Curtis, Morris & Safford, P.C.

[57] ABSTRACT

The invention relates to crop protection agents which comprise an active substance combination of herbicide and safener. The herbicides are selected from the group comprising the ALS inhibitors (ALS=acetolactate synthase) such as sulfonylureas, imidazolines, triazolopyrimidinesulfonamides, pyrimidyloxypyridinecarboxylic acid derivatives and pyrimidyloxybenzoic acid derivatives. The safeners are compounds of the formula I

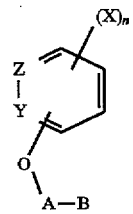

which are as defined in claim 1, where Z and Y are N or CH, it being possible for H to be replaced by X, X is H, Hal, haloalkyl or -alkoxy, alkyl, alkoxy, alkylthio, $NO_2$, $NH_2$, CN, alkylsulfonyl, A is alkylene or alkenylene, B is carboxyl or a derivative of the carboxyl group.

The mixtures are mainly suitable for controlling harmful plants in the crops maize and cereals.

11 Claims, No Drawings

MIXTURES OF HERBICIDES AND ANTIDOTES, (HETERO)-ARYLOXY COMPOUNDS, THEIR PREPARATION, COMPOSITIONS CONTAINING THEM, AND THEIR USE

This application is a continuation of application Ser. No. 08/068,416, filed May 27, 1993 now abandoned.

The invention is in the technical field of the crop protection agents, in particular of the active substance/antidote combinations, which are outstandingly suited for use against competing harmful plants in crop plants.

When agents are used for treating plants, in particular herbicides, it is possible that undesirable damage occurs on treated crop plants. However, the herbicides are not entirely compatible with (selective in) some important crop plants, such as maize or cereals, so that their use is very limited. This is why they can sometimes not be used at all, or only at application rates which are so low that the desirable broad herbicidal activity is not guaranteed. For example, a large number of herbicides of the substance classes (A) mentioned further below cannot be used selectively in maize or in cereals. It is desirable to reduce such a phytotoxicity, in particular when herbicides are applied post-emergence.

EP-A-31,938 discloses the use of aryloxycarbonitriles and aryloxycarboxamide oximes as safeners for phenoxyphenoxycarboxylates, chloroacetanilides and dimedon derivatives, EP-A-170,906 describes, inter alia, also phenoxycarboxylic acid oxime esters, and EP-A-154,153 describes aryloxy compounds as safeners for phenoxyphenoxy and heteroaryloxyphenoxy herbicides.

EP-A-112,799 mentions 4-chlorophenoxy- and 4-chloro-2-methylphenoxyacetic acid as safeners for propargyl 4-(3', 5'-dichloropyridyl-2'-oxy)-phenoxypropionate.

EP-A-293,062 describes the use of aryloxy compounds as safeners for cyclohexanedione herbicides, and, finally, EP-A-88,066 describes the use of 3,5-bis(trifluoromethyl) phenoxycarboxylic acid derivatives as safeners for, in particular, aceramides, especially tri-allate.

None of the abovementioned publications gives any indication of a potential safener action of aryloxy compounds, specifically of acetolactate synthase (ALS) inhibitors.

Novel experimental work has shown, entirely unexpectedly, that aryloxy as well as heteroaryloxy compounds are out-standingly suitable for markedly reducing, or completely compensating for, the phytotoxic secondary effects of the herbicidal active substances which act as ALS inhibitors (such as sulfonylureas, imidazolinones, triazolopyrimidinesulfonamides, pyrimidyloxypyridinecarboxylic acid derivatives and pyrimidyloxybenzoic acid derivatives; see, for example, EP-A-223,406, EP-A-249,707, EP-A-249,708, EP-A-287,072, EP-A-287,079, EP-A-321,846, EP-A-335,409, EP-A-363,040, EP-A-426,476, EP-A-435,186 and WO 91/13065) on crop plants such as maize and cereals.

The present invention therefore relates to herbicidal compositions comprising

A) at least one herbicidal active substance from the group of the sulfonylureas, imidazolinones, triazolopyrimidinesulfonemides, pyrimidyloxypyridinecarboxylic acid derivatives and pyrimidyloxybenzoic acid derivatives, B) at least one compound of the formula I

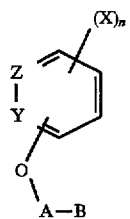

in which
Y and Z are identical or different and independently of one another are CX or N;
A is $(C_1-C_6)$-alkanediyl or $(C_3-C_8)$-alkenediyl,
B is a radical of the formula —COOR, —COSR, —CONRR$^4$,

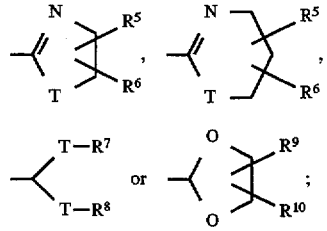

X radicals are identical or different and independently of one another are hydrogen, halogen, halo-$(C_1-C_8)$-alkyl, halo-$(C_1-C_8)$-alkoxy, $(C_1-C_8)$-alkyl, $(C_1-C_8)$-alkoxy, nitro, amino, cyano, $(C_1-C_8)$-alkylthio or $(C_1-C_8)$-alkylsulfonyl, preferably hydrogen, halogen, $(C_1-C_6)$-haloalkyl such as trifluoromethyl, $(C_1-C_6)$-haloalkoxy such as difluoromethoxy, $(C_1-C_6)$-alkyl, $(C_1-C_6)$-alkoxy, $(C_1-C_6)$-alkylthio, $(C_1-C_6)$-alkylsulfonyl, nitro, amino or cyano;
n is 3;
R is hydrogen, $(C_1-C_{18})$-alkyl, $(C_3-C_{12})$-cycloalkyl, $(C_2-C_{18})$-alkenyl, $(C_2-C_8)$-alkynyl or —N=CR$^2$R$^3$, each of the above carbon-containing radicals optionally having one or more, preferably up to three, identical or different substituents selected from the group comprising halogen, halo-$(C_1-C_8)$-alkoxy, nitro, cyano, hydroxyl, $(C_1-C_8)$-alkoxy, in which one or more, preferably up to three, CH$_2$ groups can be replaced by oxygen, $(C_1-C_8)$-alkylthio, $(C_1-C_6)$-alkylsulfinyl, $(C_1-C_6)$-alkylsulfonyl, $(C_2-C_8)$-alkenylthio, $(C_2-C_8)$-alkynylthio, $(C_2-C_8)$-alkenyloxy, $(C_2-C_8)$-alkynyloxy, $(C_3-C_7)$-cycloalkyl, $(C_3-C_7)$-cycloalkoxy, mono- and di-$(C_1-C_4)$-alkylamino, $(C_1-C_8)$-alkoxycarbonyl, $(C_2-C_8)$-alkenyloxycarbonyl, $(C_2-C_8)$-alkynyloxycarbonyl, $(C_1-C_8)$-alkylthiocarbonyl, $(C_1-C_8)$-alkylcarbonyl, $(C_2-C_8)$-alkenylcarbonyl, $(C_2-C_8)$-alkynylcarbonyl, 1-(hydroxyimino)-$(C_1-C_6)$-alkyl, 1-$(C_1-C_4)$-alkylimino-$(C_1-C_6)$-alkyl, 1-$(C_1-C_4)$-alkoxyimino-$(C_1-C_6)$-alkyl, $(C_1-C_8)$-alkylcarbonylamino, $(C_2-C_8)$-alkenylcarbonylamino, $(C_2-C_8)$-alkynylcarbonylamino, carbamoyl, $(C_1-C_8)$-alkylcarbamoyl, di-$(C_1-C_6)$-alkylcarbamoyl, $(C_2-C_6)$-alkenylcarbamoyl, $(C_2-C_6)$-alkynylcarbamoyl, $(C_1-C_8)$-alkoxycarbonylamino, $(C_1-C_8)$-alkyl-aminocarbonylamino, $(C_1-C_8)$-alkoxycarbonyloxy, $(C_1-C_8)$-alkylcarbonyloxy which is unsubstituted or preferably up to trisubstituted by halogen, nitro, $(C_1-C_4)$-alkoxy and/or optionally substituted phenyl, $(C_2-C_6)$-alkenylcarbonyloxy, $(C_2-C_6)$-alkynylcarbonyloxy, phenyl, phenyl-$(C_1-C_6)$-alkoxy, phenyl-$(C_1-C_6)$-alkoxycarbonyl, phenoxy, phenoxy-$(C_1-C_6)$-alkoxy, phenoxycarbonyl, phenoxy-$(C_1–C_6)$-alkoxycarbonyl, phenylcarbonyloxy, phenylcarbonylamino, phenyl-$(C_1–C_6)$-alkylcarbonylamino, the 10 last-mentioned radicals being unsubstituted or mono- or polysubstituted, preferably up to trisubstituted, in the phenyl ring by identical or different radicals selected from the group comprising halogen, $(C_1–C_4)$-alkyl, $(C_1–C_4)$-alkoxy, $(C_1–C_4)$-haloalkyl, $(C_1–C_4)$-haloalkoxy and nitro, —$SiR^2R^3R^4$, —O—$iR^2R^3R^4$, $R^2R^3R^4Si$—$(C_1–C_6)$-alkoxy, —CO—O—$NR^2R^3$, —O—N=$CR^2R^3$, —N=$CR^2R^3$, O—$(CH_2)_m$—$CH(OR^2)OR^3$, R'O—CHR"—CH(OR')—$(C_1–C_6)$-alkoxy and from amongst the three- to seven-membered saturated or unsaturated heterocyclic radicals which have up to three identical or different hetero atoms selected from the series comprising S, O and N and which are optionally benzo-fused and optionally substituted, preferably up to trisubstituted, by halogen and/or $(C_1–C_4)$-alkyl;

R' radicals independently of one another are $(C_1–C_4)$-alkyl, or in pairs together are a $(C_1–C_6)$-alkanediyl radical and R" is hydrogen or $(C_1–C_4)$-alkyl;

$R^2$ and $R^3$ are identical or different and independently of one another are hydrogen, optionally substituted $(C_1–C_6)$-alkyl or optionally substituted phenyl or together are an optionally substituted $(C_2–C_6)$-alkanediyl chain; and $R^4$ is hydrogen or optionally substituted $(C_1–C_4)$-alkyl; or R and $R^4$ together are an alkanediyl chain which has 2 to 5 carbon atoms and in which one $CH_2$ group can optionally be replaced by O, NH or $N(C_1–C_4)$-alkyl;

$R^5$ and $R^6$ are identical or different and independently of one another are hydrogen or $(C_1–C_6)$-alkyl;

$R^7$ and $R^8$ are identical or different and independently of one another are hydrogen or $(C_1–C_6)$-alkyl which can be substituted by halogen, $(C_1–C_4)$-alkoxy or phenyl;

$R^9$ and $R^{10}$ are identical or different and independently of one another are hydrogen or $(C_1–C_6)$-alkyl which can be substituted by halogen, $(C_1–C_4)$-alkoxy or OH;

T radicals independently of one another are oxygen or sulfur; and m is an integer from 0 to 6;

or a salt thereof.

Unless not otherwise specified individually, in the above-mentioned compounds of the formula I and hereinafter, alkyl, alkenyl and alkynyl are straight-chain or branched; the same applies analogously to the substituted alkyl, alkenyl and alkynyl radicals such as haloalkyl, hydroxyalkyl, alkoxycarbonyl and the like. Alkyl is, for example, methyl, ethyl, n- and i-propyl, n-, i-, t- and 2-butyl, pentyl radicals, hexyl radicals such as n-hexyl, i-hexyl and 1,3-dimethylbutyl, heptyl radicals such as n-heptyl, 1-methylhexyl and 1,4-dimethylpentyl; alkenyl is, for example, allyl, 1-methylprop-2-en-1-yl, 2-methyl-prop-2-en-1-yl, but-2-en-1-yl, but-3-en-1-yl, 1-methyl-but-3-enyl and 1-methyl-but-2-enyl; alkynyl is, for example, propargyl, but-2-yn-1-yl, but-3-yn-1-yl, 1-methyl-but-3-ynyl. Substituted alkyl is to be understood as meaning alkyl which is mono- or polysubstituted, preferably up to trisubstituted, in particular monosubstituted, by identical or different radicals selected from the series comprising halogen, hydroxyl and $(C_1–C_6)$-alkoxy.

Halogen is fluorine, chlorine, bromine or iodine, preferably fluorine, chlorine or bromine, in particular fluorine or chlorine. Haloalkyl, -alkenyl and -alkynyl are alkyl, alkenyl or alkynyl, each of which is partially or fully substituted by halogen, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$.

Optionally substituted phenyl is, for example, phenyl which is unsubstituted or mono- or polysubstituted, preferably up to trisubstituted, by identical or different radicals selected from the group comprising halogen, $(C_1–C_4)$-alkyl, $(C_1–C_4)$-alkoxy, $(C_1–C_4)$-haloalkyl, $(C_1–C_4)$-haloalkoxy and nitro, for example o-, m- and p-tolyl, dimethylphenyl radicals, 2-, 3- and 4-chlorophenyl, 2-, 3- and 4-trifluoro- and -trichlorophenyl, 2,4-, 3,5-, 2,5- and 2,3-dichlorophenyl, and o-, m- and p-methoxyphenyl.

A three- to seven-membered heterocyclic radical as described above is preferably derived from benzene, where at least one CH is replaced by N and/or at least two adjacent CH pairs are replaced by NH, S and/or O. The radical can be benzo-fused. It is optionally partially or fully hydrogenated. Examples of suitable radicals are, in particular, oxiranyl, pyrrolidyl, piperidyl, dioxolanyl, pyrazolyl, morpholyl, furyl, tetrahydrofuryl, indolyl, azepinyl, triazolyl, thienyl and oxazolyl.

Some compounds of the formula I contain one or more asymmetric carbon atoms or double bonds which are not mentioned separately in formula I. However, the formula I embraces all possible stereoisomers which are defined by their specific spatial shape such as enantiomers, diastereomers, E and Z isomers as well as mixtures of these.

The compounds of the formula I can form salts in which the radical R is replaced by an equivalent of an agriculturally suitable cation. Examples of these salts are metal salts, in particular alkali metal salts or alkaline earth metal salts, but also ammonium salts or salts with organic amines, and salts which contain sulfonium or phosphonium ions as cations.

Suitable salt formers are, in particular, metals and organic nitrogen bases, above all quaternary ammonium bases. Metals which are suitable for salt formation are alkaline earth metals such as magnesium or calcium, but above all alkali metals such as lithium and, in particular, potassium and sodium.

Examples of nitrogen bases which are suitable for the formation of salts are primary, secondary or tertiary, aliphatic and aromatic amines which are optionally hydroxylated on the hydrocarbon radical, such as methylamine, ethylamine, propylamine, isopropylamine, the four butylamine isomers, dimethylamine, diethylamine, dipropylamine, diisopropylamine, di-n-butylamine, pyrrolidine, piperidine, morpholine, trimethylamine, triethylamine, tripropylamine, quinuclidine, pyridine, quinoline, isoquinoline as well as methanolamine, ethanolamine, propanolamine, dimethanolamine, diethanolamine or triethanolamine.

Examples of quaternary ammonium bases are tetraalkylammonium cations in which the alkyl radicals independently of one another are straight-chain or branched $(C_1–C_6)$-alkyl groups such as the trimethylammonium cation, the tetraethylammonium cation or the trimethylethylammonium cation, and furthermore the trimethylbenzylammonium cation, the triethylbenzylammonium cation and the trimethyl-2-hydroxyethylammonium cation.

Particularly preferred as salt formers are the ammonium cation and di- as well as trialkylammonium cations in which the alkyl radicals independently of one another are straight-chain or branched $(C_1–C_6)$-alkyl groups which are optionally substituted by a hydroxyl group, such as, for example, the dimethylammonium cation, the trimethylammonium cation, the triethylammonium cation, the di(2-hydroxyethyl) ammoniumcation and the tri(2-hydroxyethyl)ammonium cation.

Preferred compositions are those in which, in the compound of the formula I,

A is $(C_1-C_4)$-alkanediyl or $(C_3-C_6)$-alkenediyl,

X radicals are identical or different and independently of one another are hydrogen, halogen, halo-$(C_1-C_6)$-alkyl, halo-$(C_1-C_6)$-alkoxy, $(C_1-C_8)$-alkyl, $(C_1-C_8)$-alkoxy, nitro, amino, cyano, $(C_1-C_6)$-alkylthio or $(C_1-C_8)$-alkylsulfonyl, preferably hydrogen, halogen, $(C_1-C_6)$-haloalkyl such as trifluoromethyl, $(C_1-C_6)$-haloalkoxy such as difluoromethoxy, $(C_1-C_6)$-alkyl, $(C_1-C_6)$-alkoxy, $(C_1-C_6)$-alkylthio, $(C_1-C_6)$-alkylsulfonyl, nitro, amino or cyano, where at least one radical X is hydrogen;

n is 3;

R is hydrogen, $(C_1-C_{12})$-alkyl, $(C_3-C_8)$-cycloalkyl, $(C_2-C_{12})$-alkenyl, $(C_2-C_8)$-alkynyl or $-N=CR^2R^3$, where each of the above carbon-containing radicals optionally has one or more, preferably up to three, identical or different substituents selected from the group comprising halogen, halo-$(C_1-C_8)$-alkoxy, nitro, cyano, hydroxyl, $(C_1-C_8)$-alkoxy in which one or more, preferably up to three, $CH_2$ groups can be replaced by oxygen, $(C_1-C_8)$-alkylthio, $(C_1-C_6)$-alkylsulfinyl, $(C_1-C_6)$-alkylsulfonyl, $(C_2-C_8)$-alkenylthio, $(C_2-C_8)$-alkynylthio, $(C_2-C_8)$-alkenyloxy, $(C_2-C_8)$-alkynyloxy, $(C_3-C_7)$-cycloalkyl, $(C_3-C_7)$-cycloalkoxy, mono- and di-$(C_1-C_4)$-alkylamino, $(C_1-C_8)$-alkoxycarbonyl, $(C_2-C_8)$-alkenyloxycarbonyl, $(C_2-C_8)$-alkynyloxycarbonyl, $(C_1-C_8)$-alkylthiocarbonyl, $(C_1-C_8)$-alkylcarbonyl, $(C_2-C_8)$-alkenylcarbonyl, $(C_2-C_8)$-alkynylcarbonyl, 1-(hydroxyimino)-$(C_1-C_6)$-alkyl, 1-$(C_1-C_4)$-alkylimino-$(C_1-C_6)$-alkyl, 1-$(C_1-C_4)$-alkoxyimino-$(C_1-C_6)$-alkyl, $(C_1-C_8)$-alkylcarbonylamino, $(C_2-C_8)$-alkenylcarbonylamino, $(C_2-C_8)$-alkynylcarbonylamino, carbamoyl, $(C_1-C_8)$-alkylcarbamoyl, di-$(C_1-C_6)$-alkylcarbamoyl, $(C_2-C_6)$-alkenylcarbamoyl, $(C_2-C_6)$-alkynylcarbamoyl-$(C_1-C_8)$-alkoxycarbonylamino, $(C_1-C_8)$-alkylaminocarbonylamino, $(C_1-C_8)$-alkoxycarbonyloxy, $(C_1-C_8)$-alkylcarbonyloxy which is unsubstituted or substituted, preferably up to trisubstituted, by halogen, nitro, $(C_1-C_4)$-alkoxy and/or optionally substituted phenyl, $(C_2-C_6)$-alkenylcarbonyloxy, $(C_2-C_6)$-alkynylcarbonyloxy, phenyl, phenyl-$(C_1-C_6)$-alkoxy, phenyl-$(C_1-C_6)$-alkoxycarbonyl, phenoxy, phenoxy-$(C_1-C_6)$-alkoxy, phenoxycarbonyl, phenoxy-$(C_1-C_6)$-alkoxycarbonyl, phenylcarbonyloxy, phenylcarbonylamino, phenyl-$(C_1-C_6)$-alkylcarbonylamino, the 10 last-mentioned radicals being unsubstituted or mono- or polysubstituted, preferably up to trisubstituted, in the phenyl ring by identical or different radicals selected from the group comprising halogen, $(C_1-C_4)$-alkyl, $(C_1-C_4)$-alkoxy, $(C_1-C_4)$-haloalkyl, $(C_1-C_4)$-haloalkoxy and nitro, $-SiR^2R^3R^4$, $-O-SiR^2R^3R^4$, $R^2R^3R^4Si-(C_1-C_6)$-alkoxy, $-CO-O-NR^2R^3$, $-O-N=CR^2R^3$, $-N=CR^2R^3$, $O-(CH_2)_m-CH(OR^2)OR^3$, $R'O-CHR''-CH(OR')-(C_1-C_6)$-alkoxy and from amongst the three- to seven-membered saturated or unsaturated heterocyclic radicals which have up to three identical or different hetero atoms selected from the series comprising S, O and N and which are optionally benzofused and optionally substituted, preferably up to trisubstituted, by halogen and/or $(C_1-C_4)$-alkyl;

R' radicals independently of one another are $(C_1-C_4)$-alkyl or in pairs together are a $(C_1-C_6)$-alkanediyl radical and R" is hydrogen or $(C_1-C_4)$-alkyl;

$R^2$ and $R^3$ are identical or different and independently of one another are hydrogen, optionally substituted $(C_1-C_6)$-alkyl or optionally substituted phenyl, or together are an optionally substituted $(C_2-C_6)$-alkanediyl chain;

$R^5$ and $R^6$ are identical or different and independently of one another are hydrogen or $(C_1-C_6)$-alkyl;

$R^7$ and $R^8$ are identical or different and independently of one another are hydrogen or $(C_1-C_6)$-alkyl which can be substituted by halogen, $(C_1-C_4)$-alkoxy or phenyl;

$R^9$ and $R^{10}$ are identical or different and independently of one another are hydrogen or $(C_1-C_6)$-alkyl which can be substituted by halogen, $(C_1-C_4)$-alkoxy or OH;

m is an integer from 0 to 6;

and the remaining radicals or variables are as defined above.

Particularly preferred compositions are those in which, in formula I,

A is $(C_1-C_3)$-alkanediyl or $(C_8-C_4)$-alkenediyl such as $CH_2$, $CH(CH_3)$, $CH_2-CH_2$, $(CH_2)_3$ or $C(CH_3)_2$;

X is as defined above and at least two radicals X are hydrogen;

n is 3;

R is hydrogen, $(C_1-C_{12})$-alkyl, $(C_3-C_8)$-cycloalkyl, $(C_2-C_{12})$-alkenyl, $(C_2-C_8)$-alkynyl or $-N=CR^2R^3$, where each of the above carbon-containing radicals optionally has one or more, preferably two, in particular one, identical or different substituents selected from the group comprising hydroxyl, $(C_1-C_8)$-alkoxy in which one or more, preferably two, in particular one, $CH_2$ group(s) can be replaced by oxygen, $(C_1-C_4)$-alkylthio, $(C_2-C_4)$-alkenylthio, $(C_2-C_4)$-alkynylthio, $(C_2-C_4)$-alkenyloxy, $(C_2-C_4)$-alkynyloxy, mono- and di-$(C_1-C_2)$-alkylamino, $(C_1-C_4)$-alkoxycarbonyl, $(C_2-C_4)$-alkenyloxycarbonyl, $(C_2-C_4)$-alkynyloxycarbonyl, $(C_1-C_4)$-alkylcarbonyl, $(C_2-C_4)$-alkenylcarbonyl, $(C_2-C_4)$-alkynylcarbonyl, $(C_1-C_4)$-alkylcarbonylamino, $(C_2-C_4)$-alkenylcarbonylamino, carbamoyl, $(C_1-C_8)$-alkylcarbamoyl, di-$(C_1-C_6)$-alkylcarbamoyl, $(C_1-C_4)$-alkoxycarbonyloxy, $(C_1-C_4)$-alkylcarbonyloxy which is unsubstituted or preferably up to disubstituted by halogen and/or $(C_1-C_4)$-alkoxy, $(C_2-C_4)$-alkenylcarbonyloxy, $(C_2-C_4)$-alkynylcarbonyloxy, phenyl, phenyl-$(C_1-C_4)$-alkoxy, phenyl-$(C_1-C_4)$-alkoxycarbonyl, phenoxy, phenoxy-$(C_1-C_4)$-alkoxy, phenoxycarbonyl, phenoxy-$(C_1-C_4)$-alkoxycarbonyl, phenylcarbonyloxy, the 8 last-mentioned radicals being unsubstituted in the phenyl ring or substituted by one or more, preferably two, identical or different radicals selected from the group comprising halogen, $(C_1-C_2)$-alkyl, $(C_1-C_2)$-alkoxy, $(C_1-C_2)$-haloalkyl, $(C_1-C_2)$-haloalkoxy and nitro, $-SiR^2R^3R^4$, $O-SiR^2R^3R^4$, $R^2R^3R^4Si-(C_1-C_4)$-alkoxy, $-O-N=CR^2R^3$, $-N=CR^2R^3$, $O-(CH_2)_m-CH(OR^2)OR^3$, $R'O-CHR''-CH(OR')-(C_1-C_6)$-alkoxy and from amongst the three-to seven-membered saturated or unsaturated heterocyclic radicals which have up to three identical or different hetero atoms selected from the series comprising S, O and N and which are optionally benzofused and optionally substituted, preferably up to trisubstituted, by halogen and/or $(C_1-C_4)$-alkyl;

R' radicals independently of one another are $(C_1-C_4)$-alkyl or in pairs together are a $(C_1-C_6)$-alkanediyl radical and R" is hydrogen or $(C_1-C_4)$-alkyl;

$R^2$ and $R^3$ are identical or different and independently of one another are hydrogen, optionally substituted $(C_1-C_6)$-alkyl or optionally substituted phenyl, or together are an optionally substituted $(C_2-C_6)$-alkanediyl chain;

$R^5$ and $R^6$ are identical or different and independently of one another are hydrogen or $(C_1-C_6)$-alkyl;

$R^7$ and $R^8$ are identical or different and independently of one another are hydrogen or $(C_1-C_6)$-alkyl which can be substituted by halogen, $(C_1-C_4)$-alkoxy or phenyl;

$R^9$ and $R^{10}$ are identical or different and independently of one another are hydrogen or $(C_1-C_6)$-alkyl which can be substituted by halogen, $(C_1-C_4)$-alkoxy or OH;

m is an integer from 0 to 2 and the remaining radicals or variables are as defined above.

The invention also relates to a method of protecting crop plants, preferably cereal or maize plants, against phytotoxic secondary effects of herbicides, which comprises applying, to the plants, the seed of the plants or the area under cultivation, an effective amount of at least one compound of the formula I before, after or simultaneously with the abovementioned herbicidal active substance.

The invention furthermore relates to the use of compounds of the formula I for protecting crop plants against phytotoxic secondary effects of the above-defined herbicides.

The invention furthermore relates to novel compounds of the formula I

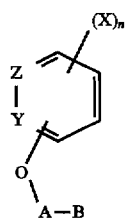
(I)

in which

Y and Z are identical or different and independently of one another are CX or N;

X radicals are identical or different and independently of one another are hydrogen, halogen, halo-$(C_1-C_8)$-alkyl, halo-$(C_1C_8)$-alkoxy, $(C_1-C_8)$-alkyl, $(C_1-C_8)$-alkoxy, nitro, amino, cyano, $(C_1-C_8)$-alkylthio or $(C_1-C_8)$-alkylsulfonyl, preferably halogen, $(C_1-C_6)$-haloalkyl such as trifluoromethyl, $(C_1-C_6)$-haloalkoxy such as difluoromethoxy, $(C_1-C_6)$-alkyl, $(C_1-C_6)$-alkoxy, $(C_1-C_6)$-alkylthio, $(C_1-C_6)$-alkylsulfonyl, nitro, amino or cyano;

n is 3;

$R^2$ and $R^3$ are identical or different and independently of one another are hydrogen, optionally substituted $(C_1-C_6)$-alkyl or optionally substituted phenyl, or together are an optionally substituted $(C_2-C_6)$-alkanediyl chain and A) in the event that at least one of the radicals Y and Z is nitrogen, then A is $(C_1-C_6)$-alkanediyl or $(C_3-C_8)$-alkenediyl;

B is a radical of the formula —COOR, —COSR, —CONRR$^4$,

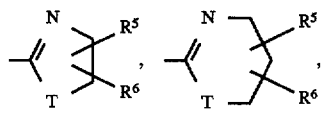

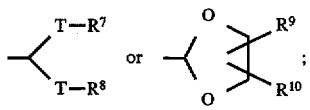

R is an equivalent of an agriculturally suitable cation, $(C_1-C_{18})$-alkyl, $(C_3-C_{12})$-cycloalkyl, $(C_3-C_{18})$-alkenyl, $(C_3-C_8)$-alkynyl or —N=CR$^2$R$^3$, where each of the above carbon-containing radicals optionally has one or more identical or different substituents selected from the group comprising halogen, halo-$(C_1-C_8)$-alkoxy, nitro, cyano, hydroxyl, $(C_1-C_8)$-alkoxy in which one or more CH$_2$ groups can be replaced by oxygen, $(C_1-C_8)$-alkylthio, $(C_1-C_6)$-alkylsulfinyl, $(C_1-C_6)$-alkylsulfonyl, $(C_2-C_8)$-alkenylthio, $(C_2-C_8)$-alkynylthio, $(C_2-C_8)$-alkenyloxy, $(C_2-C_8)$-alkynyloxy, $(C_3-C_7)$-cycloalkyl, $(C_3-C_7)$-cycloalkoxy, mono- and di-$(C_1-C_4)$-alkylamino, $(C_1-C_8)$-alkoxycarbonyl, $(C_2-C_8)$-alkenyloxycarbonyl, $(C_2-C_8)$-alkynyloxycarbonyl, $(C_1-C_8)$-alkylthiocarbonyl, $(C_1-C_8)$-alkylcarbonyl, $(C_2-C_8)$-alkenylcarbonyl, $(C_2-C_8)$-alkynylcarbonyl, 1-(hydroxyimino)-$(C_1-C_6)$-alkyl, 1-$(C_1-C_4)$-alkylimino-$(C_1-C_6)$-alkyl, 1-$(C_1-C_4)$-alkoxyimino-$(C_1-C_6)$-alkyl, $(C_1-C_8)$-alkylcarbonylamino, $(C_2-C_8)$-alkenylcarbonylamino, $(C_2-C_8)$-alkynylcarbonylamino, carbamoyl, $(C_1-C_8)$-alkylcarbamoyl, di-$(C_1-C_6)$-alkylcarbamoyl, $(C_2-C_6)$-alkenylcarbamoyl, $(C_2-C_6)$-alkynylcarbamoyl, $(C_1-C_8)$-alkoxycarbonylamino, $(C_1-C_8)$-alkylaminocarbonylamino, $(C_1-C_8)$-alkoxycarbonyloxy, $(C_1-C_8)$-alkylcarbonyloxy which is unsubstituted or substituted by halogen, nitro, $(C_1-C_4)$-alkoxy and/or optionally substituted phenyl, $(C_2-C_6)$-alkenylcarbonyloxy, $(C_2-C_6)$-alkynylcarbonyloxy, phenyl, phenyl-$(C_2-C_6)$-alkoxy, phenyl-$(C_1-C_6)$-alkoxycarbonyl, phenoxy, phenoxy-$(C_1-C_6)$-alkoxy, phenoxy-$(C_1-C_6)$-alkoxycarbonyl, phenylcarbonyloxy, phenylcarbonylamino, phenyl-$(C_1-C_6)$-alkylcarbonylamino, the 9 last-mentioned radicals being unsubstituted or mono- or polysubstituted in the phenyl ring by identical or different radicals selected from the group comprising halogen, $(C_1-C_4)$-alkyl, $(C_1-C_4)$-alkoxy, $(C_1-C_4)$-haloalkyl, $(C_1-C_4)$-haloalkoxy and nitro, —SiR$^2$R$^3$R$^4$, —O—SiR$^2$R$^3$R$^4$, R$^2$R$^3$R$^4$Si—$(C_1-C_6)$-alkoxy, —CO—O—NR$^2$R$^3$, —O—N=CR$^2$R$^3$, —N=CR$^2$R$^3$ and O—(CH$_2$)$_m$—CH(OR$^2$)OR$^3$, R'O—CHR"—CH(OR')—$(C_1-C_6)$-alkoxy, and from amongst the three- to seven-membered saturated or unsaturated heterocyclic radicals which have up to three identical or different hetero atoms from the series comprising S, O and N and which are optionally benzo-fused and optionally substituted by halogen and/or $(C_1-C_4)$-alkyl;

R ' radicals independently of one another are $(C_1-C_4)$-alkyl, or in pairs together are a $(C_1-C_6)$-alkanediyl radical and R" is hydrogen or $(C_1-C_4)$-alkyl, R$^4$ is hydrogen, optionally substituted $(C_1-C_4)$-alkyl or R and R$^4$ together are an alkanediyl chain which has 2 to 5 carbon atoms and in which one CH$_2$ group can optionally be replaced by O, NH or N$(C_1-C_4)$-alkyl, and R$^5$ and R$^6$ are identical or different and independently of one another are hydrogen or $(C_1-C_6)$-alkyl;

R$^7$ and R$^8$ are identical or different and independently of one another are hydrogen or $(C_1-C_6)$-alkyl which can be substituted by halogen, $(C_1-C_4)$-alkoxy or phenyl, R$^9$ and R$^{10}$ are identical or different and independently of one another are hydrogen or $(C_1-C_6)$-alkyl which can be substituted by halogen, $(C_1-C_4)$-alkoxy or OH, T radicals independently of one another are oxygen or sulfur, and m is an integer from 0 to 6;

B) or in the event that none of the radicals Y and Z is nitrogen,

A is $(C_1-C_6)$-alkanediyl or $(C_1-C_8)$-alkenediyl;

B is a radical of the formula —COOR, —COSR or —CONRR$^4$;

R is $(C_3-C_{18})$-alkyl, $(C_3-C_{12})$-cycloalkyl, $(C_2-C_{18})$-alkenyl or $(C_2-C_8)$-alkynyl where each of the above carbon-containing radicals has one or more identical or different substituents selected from the group comprising $(C_2-C_8)$-alkylthio, $(C_2-C_8)$-alkynylthio, $(C_2-C_8)$-alkenyloxy, $(C_2-C_8)$-alkynyloxy, $(C_3-C_7)$-cycloalkyl, $(C_3-C_7)$-cycloalkoxy, $(C_7-C_{10})$-alkenyloxycarbonyl, $(C_5-C_8)$-alkynyloxycarbonyl, $(C_1-C_8)$-alkylthiocarbonyl, $(C_2-C_8)$-alkenylcarbonyl, $(C_2-C_8)$-alkynylcarbonyl, 1-(hydroxyimino)-$(C_1-C_6)$-alkyl, 1-$(C_1-C_4)$-alkylimino-$(C_1-C_6)$-alkyl, 1-$(C_1-C_4)$-alkoxyimino-$(C_1-C_6)$-alkyl, $(C_1-C_8)$-alkylcarbonylamino, $(C_2-C_8)$-alkenylcarbonylamino, $(C_2-C_8)$-alkynylcarbonylamino, carbamoyl, $(C_1-C_8)$-alkylcarbamoyl, di-$(C_1-C_6)$-alkylcarbamoyl, $(C_2-C_6)$-alkenylcarbamoyl, $(C_2-C_6)$-alkynylcarbamoyl, $(C_1-C_8)$-alkoxycarbonylamino, $(C_1-C_8)$-alkylaminocarbonylamino, $(C_1-C_8)$-alkoxycarbonyloxy, $(C_1-C_8)$-alkylcarbonyloxy which is unsubstituted and/or substituted by halogen, nitro, $(C_1-C_4)$-alkoxy or optionally substituted phenyl, $(C_2-C_6)$-alkenylcarbonyloxy, $(C_2-C_6)$-alkynylcarbonyloxy, phenyl-$(C_2-C_6)$-alkoxy, phenyl-$(C_2-C_6)$-alkoxycarbonyl, phenoxy-$(C_1-C_6)$-alkoxy, phenoxy-$(C_2-C_6)$-alkoxycarbonyl, phenylcarbonyloxy, phenylcarbonylamino, phenyl-$(C_1-C_6)$-alkylcarbonylamino, where the 7 last-mentioned radicals are unsubstituted or mono- or polysubstituted in the phenyl ring by identical or different radicals selected from the group comprising halogen, $(C_1-C_4)$-alkyl, $(C_1-C_4)$-alkoxy, $(C_1-C_4)$-haloalkyl, $(C_1-C_4)$-haloalkoxy and nitro, —SiR$^2$R$^3$R$^4$, —O—SiR$^2$R$^3$R$^4$, R$^2$R$^3$R$^4$Si—$(C_1-C_6)$-alkoxy, —CO—O—NR$^2$R$^3$, —O—N=CR$^2$R$^3$, —N=CR$^2$R$^3$ and O—$(CH_2)_m$—CH(OR$^2$)OR$^3$-alkoxy and R'O—CHR''—CH(OR')—$(C_1-C_6)$-alkoxy, R' radicals independently of one another are $(C_1-C_4)$-alkyl, or in pairs together are a $(C_1-C_6)$-alkanediyl radical and R'' radicals are hydrogen or $(C_1-C_4)$-alkyl;

R$^4$ is hydrogen or optionally substituted $(C_1-C_4)$-alkyl;

and m is an integer from 0 to 6.

The compounds of the formula I can be prepared by generally known processes (Brettle, J. Chem. Soc. 1956, 1891; Eckstein, Roczniki Chem. 30 (1956) 633; U.S. Pat. No. 2,697,708; Newman et al., J. Am. Chem. Soc. 69 (1947) 718; M. P. Cava, N. K. Bhattacharyya, J. Org. Chem. 23 (1958) 1614; D. Heilmann, G. Kempter, Wiss. Z. P ädagog. Hochsch. "Karl Liebknecht", Potsdam 25 (1981) 35; Ger 1,099,544; U.S. Pat. No. 3,010,962).

For example, the compounds of the formula I according to the invention can be prepared in such a way that 1. a compound of the formula II

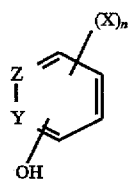

in which

Z, Y, X, n, A and B are as defined in formula I, is reacted with an alkanecarboxylic acid derivative of the formula III,

 W—A—B (III), in which

W is a leaving group;

2. an aryl- or heteroaryloxycarboxylic acid of the formula IV

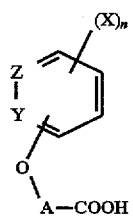 (IV)

in which

Z, Y, X, n and A are as defined in formula I, is reacted with mercaptans, amines or alcohols, or 3. an aryl- or heteroaryloxycarboxylic acid derivative of the formula V

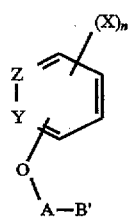 (V)

in which

Z, Y, X, n and A are as defined in formula I and B' is an alkoxycarbonyl group, is transesterified or amidated with alcohols or amines, respectively, and the resulting compounds of the formula I are, if appropriate, converted into a salt thereof.

The reactions following variant 1 are preferably carried out in dipolar aprotic solvents such as dimethyl sulfoxide, N,N-dimethylformamide or acetone, at an elevated temperature, in particular between 50° and 80° C., in the presence of a base, in particular alkali metal carbonates such as, for example, potassium carbonate.

The reactions following variant 2 are carried out either with acid catalysis, preferably with the use of sulfuric acid, or in the presence of a reagent which activates the carboxyl group such as, for example, thionyl chloride, dicyclohexylcarbodiimide or N,N'-carbonyldiimidazole, in dipolar aprotic solvents or halohydrocarbons such as, for example, chloroform or tetrachloromethane, at temperatures from room temperature to the boiling point of the reaction mixture, in particular at reflux temperature.

The transesterifications or amidations following variant 3 are principally carried out in such a way that a compound of the formula V is reacted with the alcohols or the amines at elevated temperatures, in particular at the reflux temperature of the reaction mixture, and in the presence of titanium alcoholates as catalyst.

If the compounds of the formula I according to the invention are used in subtoxic concentrations together with the herbicidal active substances or else in any desired sequence, they are capable of reducing, or completely compensating for, the phytotoxic secondary effects of these herbicides, but without reducing the efficacy of the herbicides against the harmful plants.

Examples of suitable herbicides which can be combined with the safeners according to the invention are:

A) Herbicides of the $(C_1-C_4)$alkyl, $(C_2-C_4)$alkenyl and $(C_3-C_4)$alkynyl phenoxyphenoxy- and heteroarylphenoxycarboxylate type, such as A1) phenoxyphenoxy- and benzyloxyphenoxycarboxylic acid derivatives, for example methyl 2-(4-(2,4-dichlorophenoxy)phenoxy)propionate (diclofop-methyl), methyl 2-(4-(4-bromo-2-chlorophenoxy)phenoxy) propionate (see DE-A-2,601,548), methyl 2-(4-(4-bromo-2-fluorophenoxy)phenoxy) propionate (see U.S. Pat. No. 4,808,750), methyl 2-(4-(2-chloro-4-trifluoromethylphenoxy)phenoxy) propionate (see DE-A-2,433,067), methyl 2-(4-(2-fluoro-4-trifluoromethylphenoxy)phenoxy) propionate (see U.S. Pat. No. 4,808,750), methyl 2-(4-(2,4-dichlorobenzyl)phenoxy)propionate (see DE-A-2,417,487), ethyl 4-(4-(4-trifluoromethylphenoxy)phenoxy)pent-2-ene, methyl 2-(4-(4-trifluoromethylphenoxy)phenoxy) propionate (see DE-A-2,433,067), A2) "mononuclear" heteroaryloxyphenoxyalkanecarboxylic acid derivatives, for example ethyl 2-(4-(3,5-dichloropyridyl-2-oxy)phenoxy)propionate (see EP-A-2,925), propargyl 2-(4-(3,5-dichloropyridyl-2-oxy)phenoxy) propionate (EP-A-3,114), methyl 2-(4-(3-chloro-5-trifluoromethyl-2-pyridyloxy) phenoxy)propionate (see EP-A-3,890), ethyl 2-(4-(3-chloro-5-trifluoromethyl-2-pyridyloxy) phenoxy)propionate (see EP-A-3,890), propargyl 2-(4-(5-chloro-3-fluoro-2-pyridyloxy)phenoxy) propionate (EP-A-191,736), butyl 2-(4-(5-trifluoromethyl-2-pyridyloxy)phenoxy) propionate (fusilade-butyl), A3) "binuclear" heteroaryloxyphenoxyalkanecarboxylic acid derivatives, for example methyl and ethyl 2-(4-(6-chloro-2-quinoxalyloxy)phenoxy) propionate (quizalofop-methyl and -ethyl), methyl 2-(4-(6-fluoro-2-quinoxalyloxy)phenoxy)propionate (see J. Pest. Sci. Vol. 10, 61 (1985)), 2-(4-(6-chloro-2-quinoxalyloxy)phenoxy)propionic acid and its 2-isopropylideneaminooxyethyl ester (propaquizafop and its ester), ethyl 2-(4-(6-chlorobenzoxazol-2-yl-oxy)phenoxy) propionate (fenoxaprop-ethyl), its D(+) isomer (fenoxaprop-P-ethyl)

ethyl 2-(4-(6-chlorobenzothiazol-2-yloxy) phenoxypropionate (see DE-A-2,640,730) and tetrahydrofurfur-2-ylmethyl 2-(4-(6-chloroquinoxalyloxy) phenoxypropionate (see EP-A-323,727).

B) Herbicides from the sulfonylurea series such as, for example, pyrimidine- or triazinylaminocarbonyl[benzene-, pyridine-, pyrazole-, thiophene- and (alkylsulfonyl) alkylamino-]sulfamides. Preferred substituents on the pyrimidine ring or triazine ring are alkoxy, alkyl, haloalkoxy, haloalkyl, halogen or dimethylamino, it being possible for all substituents to be combined independently of one another. Preferred substituents in the benzene, pyridine, pyrazole, thiophene or (alkylsulfonyl)alkylamino moiety are alkyl, alkoxy, halogen, nitro, alkoxycarbonyl, aminocarbonyl, alkylaminocarbonyl, dialkylaminocarbonyl, alkoxyaminocarbonyl, alkyl, alkoxyaminocarbonyl, haloalkoxy, haloalkyl, alkylcarbonyl, alkoxyalkyl and (alkanesulfonyl)alkylamino. Examples of suitable sulfonylureas are B1) phenyl- and benzylsulfonylureas and related compounds, for example 1-(2-chlorophenylsulfonyl)-3-(4-methoxy-6-methyl-1,3,5-triazin-2-yl)urea (chlorsulfuron), 1-(2-ethoxycarbonylphenylsulfonyl)-3-(4-chloro-6-methoxypyrimidin-2-yl)urea (chlorimuron-ethyl), 1-(2-methoxyphenylsulfonyl)-3-(4-methoxy-6-methyl-1,3, 5-triazin-2-yl)urea (metsulfuron-methyl), 1-(2-chloroethoxy-phenylsulfonyl)-3-(4-methoxy-6-methyl-1,3,5-triazin-2-yl)urea (triasulfuron), 1-(2-methoxycarbonylphenylsulfonyl)-3-(4,6-dimethylpyrimidin-2-yl)urea (sulfometuron-methyl), 1-(2-methoxycarbonylphenylsulfonyl)-3-(4-methoxy-6-methyl-1,3,5-triazin-2-yl)-3-methylurea (tribenuronmethyl), 1-(2-methoxycarbonylbenzylsulfonyl)-3-(4,6-dimethoxypyrimidin-2-yl)urea (bensulfuron-methyl), 1-(2-methoxycarbonylphenylsulfonyl)-3-(4,6-bis-(difluoromethoxy)pyrimidin-2-yl)urea (primisulfuron-methyl), 3-(4-ethyl-6-methoxy-1,3,5-triazin-2-yl)-1-(2,3-dihydro-1, 1-dioxo-2-methylbenzo[b]thiophene-7-sulfonyl)urea (see EP-A-79,683), 3-(4-ethoxy-6-ethyl-1,3,5-triazin-2-yl)-1-(2,3-dihydro-1,1-dioxo-2-methylbenzo[b]thiophene-7-sulfonyl)urea (see EP-A-79,683), B2) thienylsulfonylureas, for example 1-(2-methoxycarbonylthiophen-3-yl)-3-(4-methoxy-6-methyl-1,3,5-triazin-2-yl)urea (thifensulfuron-methyl), B3) pyrazolylsulfonylureas, for example 1-(4-ethoxycarbonyl-1-methylpyrazol-5-yl-sulfonyl)-3-(4, 6-dimethoxypyrimidin-2-yl)urea (pyrazosulfuronmethyl), methyl 3-chloro-5-(4,6-dimethoxypyrimidin-2-ylcarbamoylsulfamoyl)-1-methyl-pyrazole-4-carboxylate (see EP 282,613), B4) sulfonediamide derivatives, for example 3-(4,6-dimethoxypyrimidin-2-yl)-1-(N-methyl-N-methylsulfonylaminosulfonyl)urea (amidosulfuron) and structural analogues (see EP-A-0,131,258 and Z. Pfl. Krankh. Pfl. Schutz, Special Edition XII, 489–497 (1990)), B5) pyridylsulfonylureas, for example 1-(3-N,N-dimethylaminocarbonylpyridin-2-yl-sulfonyl)-3-(4,6-dimethoxypyrimidin-2-yl)urea (nicosulfuron), 1-(3-ethylsulfonylpyridin-2-yl-sulfonyl)-3-(4,6-dimethoxy-pyrimidin-2-yl)urea (DPX-E 9636, see Brighton Crop Prot. Conf.-Weeds-1989, p. 23 et seq.), pyridylsulfonylureas as they are described in DE-A-4,000, 503 and DE-A-4,030,577, preferably those of the formula

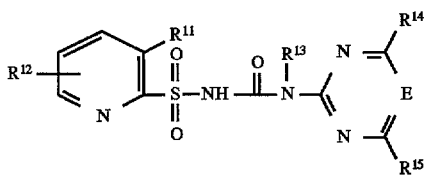

in which

E is CH or N, preferably CH, $R^{11}$ is iodine or $NR^{16}R^{17}$, $R^{12}$ is H, halogen, cyano, $C_1$-$C_3$-alkyl, $C_1$-$C_3$-alkoxy, $C_1$—$C_3$-haloalkyl, $C_1$-$C_3$-haloalkoxy, $C_1$-$C_3$-alkylthio, ($C_1$-$C_3$-alkoxy)-$C_1$-$C_3$-alkyl, ($C_1$-$C_3$-alkoxy)-carbonyl, mono- or di-($C_1$-$C_3$-alkyl)-amino, $C_1$-$C_3$-alkyl-sulfinyl or -sulfonyl, $SO_2$—$NR^aR^b$ or CO—$NR^aR^b$, in particular H, $R^a, R^b$ independently of one another are H, $C_1$-$C_3$-alkyl, $C_1$-$C_3$-alkenyl, $C_1$-$C_3$-alkynyl or together are —$(CH_2)_4$—, —$(CH_2)_5$— or $(CH_2)_2$—O—$(CH_2)_2$—, $R^{13}$ is H or $CH_3$, $R^{14}$ is halogen, $C_1$-$C_2$-alkyl, $C_1$-$C_2$-alkoxy, $C_1$-$C_2$-haloalkyl, preferably $CF_3$, $C_1$-$C_2$-haloalkoxy, preferably $OCHF_2$ or $OCH_2CF_3$, $R^{15}$ is $C_1$-$C_2$-alkyl, $C_1$-$C_2$-haloalkoxy, preferably $OCHF_2$, or $C_1$-$C_2$-alkoxy, and $R^{16}$ is $C_1$-$C_4$-alkyl and $R^{17}$ is $C_1$-$C_4$-alkylsulfonyl, or $R^{16}$ and $R^{17}$ together are a chain of the formula —$(CH_2)_3SO_2$— or —$(CH_2)_4SO_2$—, for example 3-(4,6-dimethoxypyrimidin-2-yl)-1-(3-N-methylsulfonyl-N-methylaminopyridin-2-yl)sulfonylurea or salts thereof, B6) alkoxyphenoxysulfonylureas as they are described in EP-A-0,342,569, preferably those of the formula

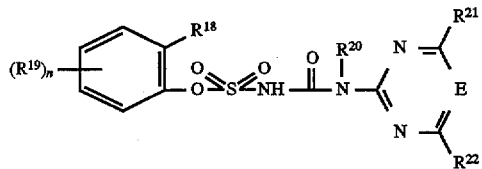

in which

E is CH or N, preferably CH, $R^{18}$ is ethoxy, propoxy or isopropoxy, $R^{19}$ is hydrogen, halogen, $NO_2$, $CF_3$, CN, $C_1$-$C_4$-alkyl, $C_1$-$C_4$-alkoxy, $C_1$-$C_4$-alkylthio or ($C_1$-$C_3$-alkoxy)-carbonyl, preferably in the 6-position on the phenyl ring, n is 1, 2 or 3, preferably 1, $R^{20}$ is hydrogen, $C_1$-$C_4$-alkyl or $C_3$-$C_4$-alkenyl, $R^{21}, R^{22}$ independently of one another are halogen, $C_1$-$C_2$-alkyl, $C_1$-$C_2$-alkoxy, $C_1$-$C_2$-haloalkyl, $C_1$-$C_2$-haloalkoxy or ($C_1$-$C_2$-alkoxy)-$C_1$-$C_2$-alkyl, preferably $OCH_3$ or $CH_3$, for example 3-(4,6-dimethoxypyrimidin-2-yl)-1-(2-ethoxyphenoxy)sulfonylurea, or salts thereof, and other related sulfonylurea derivatives and mixtures thereof.

C) Chloroacetanilide herbicides such as

N-methoxymethyl-2,6-diethylchloroacetanilide (alachlor),

N-(3'-methoxyprop-2'-yl)-2-methyl-6-ethylchloroacetanilide (metolachlor),

N-(3-methyl-1,2,4-oxadiazol-5-yl-methyl)-2,6-dimethylchloroacetanilide,

N-(2,6-dimethylphenyl)-N-(1-pyrazolylmethyl) chloroacetamide (metazachlor).

D) Thiocarbamates such as

S-ethyl N,N-dipropylthiocarbamate (EPTC) or

S-ethyl N,N-diisobutylthiocarbamate (butylate)

E) Cyclohexanedione derivatives such as methyl 3-(1-(allyloxyimino)butyl)-4-hydroxy-6,6-dimethyl-2-oxocyclohex-3-enecarboxylate (alloxydim), 2-(N-ethoxybutyrimidoyl)-5-(2-ethylthiopropyl)-3-hydroxy-2-cyclohexen-1-one (sethoxydim), 2-(N-ethoxybutyrimidoyl)-5-(2-phenylthiopropyl)-3-hydroxy-2-cyclohexen-1-one (cloproxydim), 2-(1-(3-chloroallyloxy)iminobutyl)-5-(2-(ethylthio)propyl)-3-hydroxy-2-cyclohexen-1-one, 2-(1-(3-chloroallyloxy)iminopropyl)-5-(2-(ethylthio) propyl)-3-hydroxycyclohex-2-enone (clethodim), 2-(1-allyloxyiminobutyl)-4-methoxycarbonyl-5,5-dimethyl-3-oxocyclohexenol, 2-(1-(ethoxyimino)-butyl)-3-hydroxy-5-(thian-3-yl) cyclohex-2-enone (cycloxydim), or 2-(1-ethoxyiminopropyl)-5-(2,4,6-trimethylphenyl)-3-hydroxy-2-cyclohexen-1-one (tralkoxydim).

F) 2-(4-Alkyl-5-oxo-2-imidazolin-2-yl)-benzoic acid derivatives or 2-(4-alkyl-5-oxo-2-imidazolin-2-yl) heteroarylcarboxylic acid derivatives, such as, for example, methyl 2-(4-isopropyl-4-methyl-5-oxo-2-imidazolin-2-yl)-5-methylbenzoate and 2-(4-isopropyl-4-methyl-5-oxo-2-imidazolin-2-yl)-4-methylbenzoic acid (imazamethabenz), 5-ethyl-2-(4-isopropyl-4-methyl-5-oxo-2-imidazolin-2-yl) pyridine-3-carboxylic acid (imazethapyr), 2-(4-isopropyl-4-methyl-5-oxo-2-imidazolin-2-yl) quinoline-3-carboxylic acid (imazaquin), 2-(4-isopropyl-4-methyl-5-oxo-2-imidazolin-2-yl)pyridine-3-carboxylic acid (imazapyr), or 5-methyl-2-(4-isopropyl-4-methyl-5-oxo-2-imidazolin-2-yl)pyridine-3-carboxylic acid (imazethamethapyr).

G) Triazolopyrimidinesulfonamide derivatives, for example

N-(2,6-difluorophenyl)-7-methyl-1,2,4-triazolo-(1,5-c)-pyrimidine-2-sulfonamide (flumetsulam), N-(2,6-dichloro-3-methylphenyl)-5,7-dimethoxy-1,2,4-triazolo-(1,5-c)-pyrimidine-2-sulfonamide N-(2,6-difluorophenyl)-7-fluoro-5-methoxy-1,2,4-triazolo-(1,5-c)-pyrimidine-2-sulfonamide N-(2,6-dichloro-3-methylphenyl)-7-chloro-5-methoxy-1,2,4-triazolo-(1,5-c)-pyrimidine-2-sulfonamide N-(2-chloro-6-methoxycarbonyl)-5,7-dimethyl-1,2,4-triazolo-(1,5-c)-pyrimidine-2-sulfonamide (see, for example, EP-A-343,752, U.S. Pat. No. 4,988,812).

The abovementioned herbicides from A to G are known to those skilled in the art and are described, as a rule, in "The Pesticide Manual", British Crop Protection Council, 9th Edition (1990–91) or in "Agricultural Chemicals Book II-Herbicides-", by W. T. Thompson, Thompson Publications, Fresno Calif., U.S.A. 1990 or in "Farm Chemicals Handbook '90", Meister Publishing Company, Willoughby Ohio, U.S.A. 1990.

The herbicidal active substances and the abovementioned safeners can be applied together (as a readymix or by the tank mix method) or one after the other, in any desired sequence. The ratio by weight of safener:herbicide can be varied within wide limits and is preferably in the range from 1:10 to 10:1, in particular from 1:10 to 5:1. The amounts of herbicide and safener which are optimal in each case depend on the type of the herbicide or safener used as well as on the nature of the plant stand to be treated, and they can be determined in each individual case by suitable preliminary experiments.

The safeners are applied mainly in cereal crops (wheat, rye, barley, oats), rice, maize, sorghum, but also cotton and soybeans, preferably cereals and maize.

A particular advantage of the safeners of the formula I according to the invention is found in their combination with herbicides from the group of the sulfonylureas and/or imidazolinones. Herbicides of the abovementioned structural classes primarily inhibit the key enzyme acetolactate synthase (ALS) in the plants and they are therefore related, at least partially, with regard to the mechanism of action. Some herbicides from these structural classes cannot be used, or cannot be used sufficiently selectively, in particular in cereal crops and/or maize. A combination with the safeners according to the invention allows outstanding selectivity to be achieved even with these herbicides when used in cereals or maize.

Depending on their properties, the safeners of the formula I can be used for pretreating the seed of the crop plant (seed dressing), or they can be incorporated into the seed furrows prior to sowing, or used together with the herbicide prior to, or after, plant emergence. Pre-emergence treatment includes both treatment of the area under cultivation prior to sowing and treatment of the areas under cultivation where seed has been sown but growth of the crop plants has not yet taken place. The application together with the herbicide is preferred. Tank mixes or readymixes can be employed for this purpose.

Depending on the indication and on the herbicide used, the application rates of safeners required can vary within wide limits and they are, as a rule, in the range from 0.001 to 5 kg, preferably 0.005 to 0.5 kg, of active substance per hectare.

The present invention thus also relates to a method for protecting crop plants against phytotoxic secondary effects of herbicides, which comprises applying, to the plants, the seeds of the plants or the area under cultivation, an effective amount of a compound of the formula I before, after or simultaneously with the herbicide.

The invention also relates to crop protection agents comprising an active substance of the formula I and customary formulation auxiliaries, as well as to herbicidal compositions comprising an active substance of the formula I and a herbicide as well as formulation auxiliaries conventionally used in the field of crop protection.

The compounds of the formula I and combinations thereof with one or more of the abovementioned herbicides can be formulated in various ways, depending on the prevailing biological and/or chemical-physical parameters. Examples of possible formulations which are suitable are: wettable powders (WP), emulsifiable concentrates (EC), water-soluble powders (SP), water-soluble concentrates (SL), concentrated emulsions (EW) such as oil-in-water and water-in-oil emulsions, sprayable solutions or emulsions, capsule suspensions (CS), dispersions on an oil or water basis (SC), suspoemulsions, suspension concentrates, dusts (DP), oil-miscible solutions (OL), seed-dressing agents, granules (GR) in the form of microgranules, spray granules, coated granules and adsorption granules, granules for soil application or for scattering, water-soluble granules (SG), water-dispersible granules (WG), ULV formulations, microcapsules and waxes.

These individual formulation types are known in principle and described, for example, in: Winnacker-Küchler, "Chemische Technologie" [Chemical Technology], Volume 7, C. Hauser Verlag Munich, 4th Ed. 1986; Wade van Valkenburg, "Pesticide Formulations", Marcel Dekker New York, 1973; K. Martens, "Spray Drying Handbook", 3rd Ed. 1979, G. Goodwin Ltd., London.

The necessary formulation auxiliaries such as inert materials, surfactants, solvents and other additives are equally known and described, for example, in: Watkins, "Handbook of Insecticide Dust Diluents and Carriers", 2nd Ed., Darland Books, Caldwell New Jersey; H.v.Olphen "Introduction to Clay Colloid Chemistry", 2nd Ed., J. Wiley & Sons, New York, Marsden "Solvents Guide", 2nd Ed., Interscience, New York 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., New York 1964; Schönfeldt, "Grenzfl ächenaktive Äthylenoxidaddukte" [Surface-Active Ethylene Oxide Adducts], Wiss. Verlagsgesell., Stuttgart 1976; Winnacker-Küchler "Chemische Technologie" [Chemical Technology], Volume 7, C. Hauser Verlag Munich, 4th Ed. 1986.

Based on these formulations, it is also possible to prepare combinations with other pesticidally active substances, fertilizers and/or growth regulators, for example in the form of a readymix or a tank mix.

Wettable powders or preparations which are uniformly dispersible in water and which, besides the active substance, also contain wetting agents, for example polyoxethylated alkylphenols, polyoxethylated fatty alcohols and fatty a mines, fatty alcohol polyglycol ether sulfates, alkanesulfonates or alkylarylsulfonates, and dispersing agents, for example sodium ligninsulfonate, sodium 2,2-dinaphthylmethane-6,6'-disulfonate, sodium dibutylnaphthalenesulfonate, or else sodium oleoylmethyltaurinate, in addition to a diluent or inert substance.

Emulsifiable concentrates are prepared by dissolving the active substance in an organic solvent, for example butanol, cyclohexanone, dimethylformamide, xylene, or else higher boiling aromatics or hydrocarbons, with the addition of one or more emulsifiers. Examples of emulsifiers which can be used are: calcium alkylarylsulfonates such as calcium dodecylbenzenesulfonate, or non-ionic emulsifiers such as fatty acid polyglycol esters, alkylaryl polyglycol ethers, fatty alcohol polyglycol ethers, propylene oxide/ethylene oxide condensation products (for example block copolymers), alkyl polyethers, sorbitan fatty acid esters, polyoxyethylene sorbitan fatty acid esters or polyoxethylene sorbitol esters.

Dusts are obtained by grinding the active substance with finely divided solid substances, for example talc, natural clays such as kaolin, bentonite and pyrophyllite, or diatomaceous earth.

Granules can be prepared either by spraying the active substance onto adsorptive, granulated inert material or by applying active substance concentrates onto the surface of carriers such as sand, kaolinites or granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

The agrochemical preparations comprise, as a rule, 0.1 to 99 percent by weight, in particular 0.1 to 95% by weight, of active substances of the formula I (antidote) or of the mixture of antidote/herbicidal active substance, and 1 to 99.9% by weight, in particular 5 to 99.8% by weight, of a solid or liquid additive, and 0 to 25% by weight, in particular 0.1 to 25% by weight, of a surfactant.

The active substance concentration in wettable powders is, for example, about 10 to 90% by weight, the remainder to 100% by weight is composed of conventional formulation components. In the case of emulsifiable concentrates, the active substance concentration is about 1 to 80% by weight of active substances. Formulations in the form of dusts comprise about 1 to 20% by weight of active substances, sprayable solutions approximately 0.2 to 20% by weight of active substances. In the case of granules, such as water-dispersible granules, the active substance content depends partly on whether the active compound is in liquid or solid form. In general, the water-dispersible granules contain between 10 and 90% by weight of active substances.

In addition, the active substance formulations mentioned comprise, if appropriate, the adhesives, wetting agents, dispersants, emulsifiers, penetrants, solvents, fillers or carriers which are conventional in each case.

For use, the formulations which are present in commercially available form are diluted, if appropriate, in a conventional manner, for example using water in the case of wettable powders, emulsifiable concentrates, dispersions and water-dispersible granules. Preparations in the form of dusts, granules as well as sprayable solutions are usually not further diluted with other inert substances before use. The application rate of the antidotes required varies with the external conditions such as, inter alia, temperature, humidity and the nature of the herbicide used.

The Examples which follow are intended to illustrate the invention:

A. Formulation Examples a) A dust is obtained by mixing 10 parts by weight of a compound of the formula I, or of an active substance mixture of a herbicide and a compound of the formula I, and 90 parts by weight of talc as inert substance and comminuting the mixture in a hammer mill.

b) A wettable powder which is readily dispersible in water is obtained by mixing 25 parts by weight of a compound of the formula I, or of an active substance mixture of a herbicide and a safener of the formula I, 64 parts by weight of kaolin-containing quartz as inert substance, 10 parts by weight of potassium ligninsulfonate and 1 part by weight of sodium oleoylmethyl taurinate as wetting and dispersing agent, and grinding the mixture in a pinned-disk mill.

c) A dispersion concentrate which is readily dispersible in water is obtained by mixing 20 parts by weight of a compound of the formula I, or of an active substance mixture of a herbicide and a safener of the formula I, 6 parts by weight of alkylphenol polyglycol ether (®Tritonx 207), 3 parts by weight of isotridecanol polyglycol ether (8 EO) and 71 parts by weight of paraffinic mineral oil (boiling range, for example, about 255° to above 277° C.) and grinding the mixture in a ball mill to a fineness of below 5 microns.

d) An emulsifiable concentrate is obtained from 15 parts by weight of a compound of the formula I, or of an active substance mixture of a herbicide and a safener of the formula I, 75 parts by weight of cyclohexanone as solvent and 10 parts by weight of oxethylated nonylphenol as emulsifier.

e) Water-dispersible granules are obtained by mixing

| 75 parts by weight | of a compound of the formula I or of an active substance mixture of a herbicide and a safener of the formula I, |
|---|---|
| 10 " | of calcium ligninsulfonate, |
| 5 " | of sodium lauryl sulfate, |
| 3 " | of polyvinyl alcohol and |
| 7 " | of kaolin, | grinding the mixture in a pinned-disk mill and granulating the powder in a fluidized bed by spraying on water as granulation liquid.

f) Water-dispersible granules are also obtained by homogenizing and precomminuting, on a colloid mill,

| 25 parts by weight | of a compound of the formula I, or of an active substance mixture of a herbicide and a safener of the formula I, |
|---|---|
| 5 " | of sodium 2,2'-dinaphthylmethane-6,6'-disulfonate, |
| 2 " | of sodium oleoyl methyl taurinate, |
| 1 " | of polyvinyl alcohol, |
| 17 " | parts by weight of calcium carbonate and |
| 50 " | of water, | subsequently grinding the mixture in a bead mill, and atomizing and drying the resulting suspension in a spray tower by means of a single-substance nozzle.

B. Preparation Examples:

1. (1-Methyl)hexyl 2-pyridyloxyacetate (Example 82 of Table 1)

5.0 g (28 mmol) of ethyl 2-pyridyloxyacetate were suspended in 100 ml of 2-heptanol, 1 ml of titanium tetraisopropoxide were added, and the mixture was stirred for 4 hours at 120° C. The excess 2-heptanol was subsequently distilled off under an oil pump vacuum, and the residue was purified by column chromatography. 6.2 g (90% of theory) of (1-methyl)hexyl 2-pyridyloxyacetate were obtained as a colorless oil.

2. Ethyl 2,4-dichlorophenoxyacetate (Example 17 of Table 1)

1.3 g (14 mmol) of $H_2SO_4$ were added to 15.0 g (68 mmol) of 2,4-dichlorophenoxyacetic acid in 20 ml of ethanol, and the mixture was refluxed for 5 hours. The mixture was subsequently concentrated in vacuo, the residue was poured into 100 ml of ice-water, the organic phase was separated off, and the aqueous phase was extracted using ether. The combined organic phases were washed using 2N $Na_2CO_3$ solution and water, dried over magnesium sulfate and concentrated. 8.9 g (53% of theory) of ethyl 2,4-dichlorophenoxyacetate were obtained as a colorless oil.

A series of compounds of the following formula I are listed in Table 1 below by way of example. Unless otherwise indicated in the fourth column, X is in each case hydrogen.

Table 1

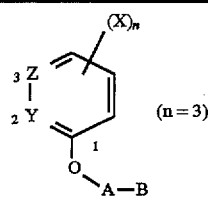

(n = 3)

| Ex. | Y | Z | X | −A−B | m.p. |
|---|---|---|---|---|---|
| 1 | CX | CX | 4-Cl | −CH$_2$−COO−H | |
| 2 | CX | CX | 4-Cl | −CH$_2$−COO−C$_2$H$_5$ | |
| 3 | CX | CX | 4-Cl | −CH$_2$−COO−CH$_2$−CH=CH$_2$ | oil |
| 4 | CX | CX | 4-Cl | −CH$_2$−COO−CH(CH$_3$)−(CH$_2$)$_4$−CH$_3$ | oil |
| 5 | CX | CX | 4-Cl | −CH$_2$−COO−(CH$_2$)$_2$−O−CO−CH$_3$ | oil |
| 6 | CX | CX | 4-Cl | −CH$_2$−COO−C$_2$H$_5$−O−C$_4$H$_9$(n) | oil |
| 7 | CX | CX | 4-Cl | −CH$_2$−COO−C$_4$H$_9$(n) | oil |
| 8 | CX | CX | 4-Cl | −CH$_2$−COO−C$_8$H$_{17}$(i) | |
| 9 | CX | CX | 4-Cl | −CH$_2$−COONa | |
| 10 | CX | CX | 4-Cl | −CH$_2$−COOK | |
| 11 | CX | CX | 4-Cl | −CH$_2$−COONH$_4$ | |
| 12 | CX | CX | 4-Cl | −CH$_2$−COONH$_2$(CH$_3$)$_2$ | |
| 13 | CX | CX | 4-Cl | −CH$_2$−COONH$_3$(C$_7$H$_{15}$) | |
| 14 | CX | CX | 4-Cl | −CH$_2$−COONH$_2$(C$_2$H$_5$OH)$_2$ | |
| 15 | CX | CX | 4-Cl | −CH$_2$−COONH(C$_2$H$_5$OH)$_3$ | |
| 16 | CX | CX | 2,4-Di-Cl | −CH$_2$−COO−H | |
| 17 | CX | CX | 2,4-Di-Cl | −CH$_2$−COO−C$_2$H$_5$ | oil |
| 18 | CX | CX | 214-Di-Cl | −CH$_2$−COO−CH$_2$−CH=CH$_2$ | oil |
| 19 | CX | CX | 2,4-Di-Cl | −CH$_2$−COO−CH(CH$_3$)−(CH$_2$)$_4$−CH$_3$ | oil |
| 20 | CX | CX | 2,4-Di-Cl | −CH$_2$−COO−C$_2$H$_5$−O−C$_4$H$_9$(n) | oil |
| 21 | CX | CX | 2,4-Di-Cl | −CH$_2$−COO−C$_4$H$_9$(n) | oil |
| 22 | CX | CX | 2,4-Di-Cl | −CH$_2$−COO−C$_8$H$_{17}$(i) | |
| 23 | CX | CX | 2,4-Di-Cl | −CH$_2$−COONa | |
| 24 | CX | CX | 2,4-Di-Cl | −CH$_2$−COOK | |
| 25 | CX | CX | 2,4-Di-Cl | −CH$_2$−COONH$_4$ | |
| 26 | CX | CX | 2,4-Di-Cl | −CH$_2$−COONH$_2$(CH$_3$)$_2$ | |
| 27 | CX | CX | 2,4-Di-Cl | −CH$_2$−COONH$_3$(C$_7$H$_{15}$) | |
| 28 | CX | CX | 2,4-Di-Cl | −CH$_2$−COONH$_2$(C$_2$H$_5$OH)$_2$ | |
| 29 | CX | CX | 2,4-Di-Cl | −CH$_2$−COONH(C$_2$H$_5$OH)$_3$ | |
| 30 | CX | CX | 3,4-Di-Cl | −CH$_2$−COO−H | |
| 31 | CX | CX | 3,4-Di-Cl | −CH$_2$−COO−C$_2$H$_5$ | |
| 32 | CX | CX | 3,4-Di-Cl | −CH$_2$−COO−CH$_2$−CH=CH$_2$ | |
| 33 | CX | CX | 3,4-Di-Cl | −CH$_2$−COO−C$_2$H$_5$−O−C$_4$H$_9$(n) | oil |
| 34 | CX | CX | 3,4-Di-Cl | −CH$_2$−COO−CH(CH$_3$)−(CH$_2$)$_4$−CH$_3$ | oil |
| 35 | CX | CX | 2-CH$_3$, 4-Cl | −CH(CH$_3$)−COO−H | |
| 36 | CX | CX | 2-CH$_3$, 4-Cl | −CH(CH$_3$)−COO−C$_2$H$_5$ | |
| 37 | CX | CX | 2-CH$_3$, 4-Cl | −CH$_2$−COO−CH(CH$_3$)−(CH$_2$)$_4$−CH$_3$ | oil |
| 38 | CX | CX | 2,4-Di-Cl | −(CH$_2$)$_3$−COO−H | |
| 39 | CX | CX | 2,4-Di-Cl | −(CH$_2$)$_3$−COO−C$_2$H$_5$ | oil |
| 40 | CX | CX | 2,4-Di-Cl | −(CH$_2$)$_3$−COO−CH(CH$_3$)−(CH$_2$)$_4$−CH | oil |
| 41 | CX | CX | 4-F | −CH$_2$−COO−H | |
| 42 | CX | CX | 4-F | −CH$_2$−COO−C$_2$H$_5$ | |
| 43 | CX | CX | 4-F | −CH$_2$−COO−CH(CH$_3$)−(CH$_2$)$_4$−CH$_3$ | oil |
| 44 | CX | CX | 4-F | −CH$_2$−COO−CH$_2$−CH=CH$_2$ | |
| 45 | CX | CX | 4−CH$_3$ | −CH$_2$−COO−C$_2$H$_5$ | |
| 46 | CX | CX | 4−CH$_3$ | −CH$_2$−COO−CH(CH$_3$)−(CH$_2$)$_4$−CH$_3$ | |
| 47 | CX | CX | 4-OC$_2$H$_5$ | −CH$_2$−COO−C$_2$H$_5$ | |
| 48 | CX | CX | 4-OC$_2$H$_5$ | −CH$_2$−COO−CH(CH$_3$)−(CH$_2$)$_4$−CH$_3$ | oil |
| 49 | CX | CX | 2-Cl, 4-CF$_3$ | −CH$_2$−COO−H | |
| 50 | CX | CX | 2-Cl, 4-CF$_3$ | −CH$_2$−COO−C$_2$H$_5$ | |
| 51 | CX | CX | 2-Cl, 4-CF$_3$ | −CH$_2$−COO−CH(CH$_3$)−(CH$_2$)$_4$−CH$_3$ | oil |
| 52 | CX | CX | 4-Br | −CH$_2$−COO−C$_2$H$_5$ | oil |
| 53 | CX | CX | 4-Br | −CH$_2$−COO−CH$_3$ | oil |
| 54 | CX | CX | 4-Br | −CH$_2$−COO−CH(CH$_3$)−(CH$_2$)$_4$−CH$_3$ | oil |
| 55 | CX | CX | 3-Br | −CH$_2$−COO−CH$_3$ | |
| 56 | CX | CX | 3-Br | −CH$_2$−COO−CH(CH$_3$)−(CH$_2$)$_4$−CH$_3$ | oil |
| 57 | CX | CX | 2-F | −CH$_2$−COO−C$_2$H$_5$ | |
| 58 | CX | CX | 2-F | −CH$_2$−COO−CH(CH$_3$)−(CH$_2$)$_4$−CH$_3$ | oil |
| 59 | CX | CX | 4-CH(CH$_3$)$_2$ | −CH$_2$−COO−C$_2$H$_5$ | |
| 60 | CX | CX | 4-CH (CH$_3$)$_2$ | −CH$_2$−COO−CH(CH$_3$)−(CH$_2$)$_4$−CH$_3$ | |
| 61 | CX | CX | 3-CF$_3$ | −CH$_2$−COO−C$_2$H$_5$ | |
| 62 | CX | CX | 3-CF$_3$ | −CH$_2$−COO−CH(CH$_3$)−(CH$_2$)$_4$−CH$_3$ | oil |
| 63 | CX | CX | 4-I | −CH$_2$−COO−C$_2$H$_5$ | 61° C. |
| 64 | CX | CX | 4-I | −CH$_2$−COO−CH(CH$_3$)−(CH$_2$)$_4$−CH$_3$ | oil |
| 65 | CX | CX | 3-I | −CH$_2$−COO−C$_2$H$_5$ | oil |
| 66 | CX | CX | 3-I | −CH$_2$−COO−CH(CH$_3$)−(CH$_2$)$_4$−CH$_3$ | oil |
| 67 | CX | CX | 4-NO$_2$ | −CH$_2$−COO−C$_2$H$_5$ | 76° C. |

Table 1-continued

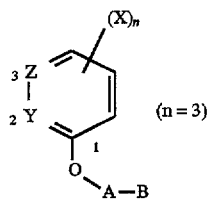
(n = 3)

| Ex. | Y | Z | X | −A−B | m.p. |
|---|---|---|---|---|---|
| 68 | CX | CX | 4-NO$_2$ | −CH$_2$−COO−CH(CH$_3$)−(CH$_2$)$_4$−CH$_3$ | oil |
| 69 | N | CX | 4,6-Di-Cl | −CH$_2$−COO−C$_2$H$_5$ | |
| 70 | N | CX | 4,6-Di-Cl | −CH$_2$−COO−CH(CH$_3$)−(CH$_2$)$_4$−CH$_3$ | |
| 71 | N | CX | 4,6-Di-Cl | −CH$_2$−COO−H | |
| 72 | CX | N | 2,4-Di-Cl | −CH$_2$−COO−H | |
| 73 | CX | N | 2,4-Di-Cl | −CH$_2$−COO−C$_2$H$_5$ | |
| 74 | CX | N | 2,4-Di-Cl | −CH$_2$−COO−CH(CH$_3$)−(CH$_2$)$_4$−CH$_3$ | |
| 75 | CX | N | 2-Cl | −CH$_2$−COO−H | |
| 76 | CX | N | 2-Cl | −CH$_2$−COO−C$_2$H$_5$ | |
| 77 | CX | N | 2-Cl | −CH$_2$−COO−CH(CH$_3$)−(CH$_2$)$_4$−CH$_3$ | |
| 78 | N | CX | 4-Cl, 6-F | −CH$_2$−COO−H | |
| 79 | N | CX | 4-Cl, 6-F | −CH$_2$−COO−C$_2$H$_5$ | |
| 80 | N | CX | 4-Cl, 6-F | −CH$_2$−COO−CH(CH$_3$)−(CH$_2$)$_4$−CH$_3$ | |
| 81 | N | CX | | −CH$_2$−COO−C$_2$H$_5$ | |
| 82 | N | CX | | −CH$_2$−COO−CH(CH$_3$)−(CH$_2$)$_4$−CH$_3$ | |
| 83 | CX | CX | 4-Cl | −CH$_2$−COO−CH(CH$_3$)−CH$_2$−O−CH$_2$−CH=CH$_2$ | oil |
| 84 | CX | CX | 4-Br | −CH$_2$−COO−CH(CH$_3$)−CH$_2$−O−CH$_2$−CH=CH$_2$ | |
| 85 | CX | CX | 2,4-Di-Cl | −CH$_2$−COO−CH(CH$_3$)−CH$_2$−O−CH$_2$−CH=CH$_2$ | |
| 86 | CX | CX | 3,4-Di-Cl | −CH$_2$−COO−CH(CH$_3$)−CH$_2$−O−CH$_2$−CH=CH$_2$ | |
| 87 | CX | CX | 4-F | −CH$_2$−COO−CH(CH$_3$)−CH$_2$−O−CH$_2$−CH=CH$_2$ | |
| 88 | CX | CX | 4-CF$_3$ | −CH$_2$−COO−CH(CH$_3$)−CH$_2$−O−CH$_2$−CH=CH$_2$ | |
| 89 | CX | CX | 3-CF$_3$ | −CH$_2$−COO−CH(CH$_3$)−CH$_2$−O−CH$_2$−CH=CH$_2$ | |
| 90 | CX | CX | 2-Cl, 4-CF$_3$ | −CH$_2$−COO−CH(CH$_3$)−CH$_2$−O−CH$_2$−CH=CH$_2$ | |
| 91 | CX | CX | 4-Cl | −CH$_2$−COO−(CH$_2$)$_2$−O−CO−CH(CH$_3$)$_2$ | |
| 92 | CX | CX | 4-Cl | −CH$_2$−COO−(CH$_2$)$_2$−O−CO−C(CH$_3$)$_3$ | |
| 93 | CX | CX | 4-Cl | −CH$_2$−COO−(CH$_2$)$_3$−O−CO−CH(CH$_3$)$_3$ | |
| 94 | CX | CX | 4-Cl | −CH$_2$−COO−(CH$_2$)$_3$−O−CO−CH$_3$ | |
| 95 | CX | CX | 2,4-Di-Cl | −CH$_2$−COO−(CH$_2$)$_2$−O−CO−C(CH$_3$)$_3$ | |
| 96 | CX | CX | 2,4-Di-Cl | −CH$_2$−COO−(CH$_2$)$_2$−O−CO−CH(CH$_3$)$_2$ | |
| 97 | CX | CX | 2,4-Di-Cl | −CH$_2$−COO−(CH$_2$)$_2$−O−CO−C(CH$_3$)$_3$ | |
| 98 | CX | CX | 2,4-Di-Cl | −CH$_2$−COO−(CH$_2$)$_3$−O−CO−CH$_3$ | |
| 99 | CX | CX | 2-CH$_3$, 4-Cl | −CH(CH$_3$)−COO−CH(CH$_3$)−(CH$_2$)$_4$−CH$_3$ | |
| 100 | CX | CX | 2-CH$_3$, 4-Cl | −CH$_2$−COO−H | |
| 101 | CX | CX | 2-CH$_3$, 4-Cl | −CH$_2$−COO−C$_2$H$_5$ | |
| 102 | CX | CX | 2-CH$_3$, 4-Cl | −CH$_2$−COO−C$_8$H$_{17}$(i) | |
| 103 | CX | CX | 4-Cl | −CH$_2$−COO−(CH$_2$)$_2$−O−COCF$_3$ | oil |
| 104 | CX | CX | 4-Cl | −CH$_2$−COO−(CH$_2$)$_3$−O−COCF$_3$ | |
| 105 | CX | CX | 3,4-Di-Cl | −CH$_2$−COO−(CH$_2$)$_2$−O−COCF$_3$ | |
| 106 | CX | CX | 3,4-Di-Cl | −CH$_2$−COO−(CH$_2$)$_3$−O−COCF$_3$ | |
| 107 | CX | CX | 4-Cl | −CH$_2$−COO−(CH$_2$)$_2$−NH−COCH$_3$ | |
| 108 | CX | CX | 4-Cl | −C(CH$_3$)$_2$−COO−C$_2$H$_5$ | |
| 109 | CX | CX | 4-Cl | −C(CH$_3$)$_2$−COO−CH(CH$_3$)−(CH$_2$)$_4$−CH$_3$ | |
| 110 | CX | CX | 4-Cl | −CH$_2$−COO−(CH$_2$)$_2$−O−CO−OC$_2$H$_5$ | |
| 111 | CX | CX | 4-Cl | −CH$_2$−COO−CH$_2$−COO−C$_2$H$_5$ | |
| 112 | N | N | 4-Cl | −CH$_2$−COO−H | 260° C. |
| 113 | N | N | 4-Cl | −CH$_2$−COO−CH$_3$ | 93° C. |
| 114 | N | N | 4-Cl | −CH$_2$−COO−CH(CH$_3$)−(CH$_2$)$_4$−CH$_3$ | |
| 115 | N | N | 4-Cl | −CH$_2$−COO−CH(CH$_3$)−CH$_2$−O−CH$_2$−CH=CH$_2$ | |
| 116 | N | CX | 4-Cl | −CH$_2$−COO−H | 130° C. |
| 117 | N | CX | 4-Cl | −CH$_2$−COO−C$_2$H$_5$ | 33° C. |
| 118 | N | CX | 4-Cl | −CH$_2$−COO−CH(CH$_3$)−(CH$_2$)$_4$−CH$_3$ | |
| 119 | N | CX | 4-Cl | −CH$_2$−COO−CH(CH$_3$)−CH$_2$−O−CH$_2$−CH=CH$_2$ | |
| 120 | CX | CX | 2,4-Di-Cl | −CH$_2$−COO−(CH$_2$)$_2$−O−CO−CF$_3$ | oil |
| 121 | CX | CX | 2,4-Di-Cl | −CH$_2$−COO−CH$_2$−S−CH$_3$ | oil |
| 122 | CX | CX | 2,4-Di-Cl | −CH$_2$−COO−CH$_2$−SO$_2$−CH$_3$ | 120° C. |
| 123 | CX | CX | 4-Br | −CH$_2$−COO−C$_3$H$_7$ (n) | oil |
| 124 | CX | CX | 4-Br | −CH$_2$−COO−C$_3$H$_7$ (i) | oil |
| 125 | CX | CX | 4-Br | −CH$_2$−COO−CH$_2$−CH=CH$_2$ | oil |
| 126 | CX | CX | 4-Br | −CH$_2$−COO−C$_6$H$_{17}$ (i) | |
| 127 | CX | CX | 4-Br | −CH$_2$−COO−C$_4$H$_9$ (n) | |
| 128 | CX | CX | 4-Br | −CH$_2$−COO−(CH$_2$)$_2$−O−CO−CH$_3$ | |
| 129 | CX | CX | 4-Br | −CH$_2$−COO−(CH$_2$)$_2$−O−CO−C(CH$_3$)$_3$ | |
| 130 | CX | CX | 4-Br | −CH$_2$−COO−(CH$_2$)$_2$−O−CO−CF$_3$ | |
| 131 | CX | CX | 4-Br | −CH$_2$−COO−(CH$_2$)$_3$−O−CO−CH$_3$ | |
| 132 | CX | CX | 4-Br | −(CH$_2$)$_3$−COO−C$_2$H$_5$ | |
| 133 | CX | CX | 4-Br | −(CH$_2$)$_3$−COO−CH(CH$_3$)−(CH$_2$)$_4$−CH$_3$ | |
| 134 | CX | CX | 4-CF$_3$ | −CH$_2$−COO−C$_2$H$_5$ | |

Table 1-continued $$\underset{2}{\overset{3}{Y}}\underset{}{\overset{Z}{\bigcirc}}\underset{1}{\overset{(X)_n}{\bigg|}}\quad (n=3)$$
$$\underset{A-B}{O}$$

| Ex. | Y | Z | X | —A—B | m.p. |
|---|---|---|---|---|---|
| 135 | CX | CX | 4-CF₃ | —CH₂—COO—CH(CH₃)—(CH₂)₄—CH₃ | |
| 136 | CX | CX | 4-Cl | —(CH₂)₃—COO—C₂H₅ | oil |
| 137 | CX | CX | 4-Cl | —(CH₂)₃—COO—CH(CH₃)—(CH₂)₄—CH₃ | oil |
| 138 | CX | CX | 2,4-Di-Br | —CH₂—COO—C₂H₅ | 39° C. |
| 139 | CX | CX | 2,4-Di-Br | —CH₂—COO—CH(CH₃)—(CH₂)₄—CH₃ | oil |
| 140 | CX | CX | 4-CN | —CH₂—COO—C₂H₅ | 55° C. |
| 141 | CX | CX | 4-CN | —CH₂—COO—CH(CH₃)—(CH₂)₄—CH₃ | oil |
| 142 | CX | CX | 4-CF₃ | —(CH₂)₃—COO—C₂H₅ | |
| 143 | CX | CX | 4-CF₃ | —(CH₂)₃—COO—CH(CH₃)—(CH₂)₄—CH₃ | |
| 144 | CX | CX | 4-CF₃ | —CH₂—COO—(CH₂)₂—O—CO—CH₃ | |
| 145 | CX | CX | 4-CF₃ | —CH₂—COO—(CH₂)₃—O—CO—CH₃ | |
| 146 | CX | CX | 4-CF₃ | —CH₂—COO—(CH₂)₂—O—CO—C(CH₃)₃ | |
| 147 | CX | CX | 4-CF₃ | —CH(CH₃)—COO—C₂H₅ | |
| 148 | CX | CX | 4-CF₃ | —CH(CH₃)—COO—CH(CH₃)—(CH₂)₄—CH₃ | |
| 149 | CX | CX | 4-CF₃ | —CH₂—COO—CH₂—CH=CH₂ | |
| 150 | CX | CX | 4-CF₃ | —CH(CH₃)—COO—CH₂—CH=CH₂ | |
| 151 | CX | CX | 4-CF₃ | —(CH₂)₃—COO—CH₂—CH=CH₂ | |
| 152 | CX | CX | 2-Cl, 4-CF₃ | —CH₂—COO—(CH₂)₂—O—CO—CH₃ | |
| 153 | CX | CX | 2-Cl, 4-CF₃ | —CH₂—COO—(CH₂)₃—O—CO—CH₃ | |
| 154 | CX | CX | 2-Cl, 4-CF₃ | —CH₂—COO—(CH₂)₂—O—CO—C(CH₃)₃ | |
| 155 | CX | CX | 2-Cl, 4-CF₃ | —(CH₂)₃—COO—C₂H₅ | |
| 156 | CX | CX | 2-Cl, 4-CF₃ | —(CH₂)₃—COO—CH(CH₃)—(CH₂)₄—CH₃ | |
| 157 | CX | CX | 2-Cl, 4-CF₃ | —(CH₂)₃—COO—CH₂—CH=CH₂ | |
| 158 | CX | CX | 2-Cl, 4-CF₃ | —CH₂—COO—CH₂—CH=CH₂ | |
| 159 | CX | CX | 2-Cl, 4-CF₃ | —CH₂—COO—C₃H₇ (n) | |
| 160 | CX | CX | 2-Cl, 4-CF₃ | —CH₂—COO—C₃H₇ (i) | |

C. Biological Examples:

EXAMPLE 1

Wheat and barley were grown in plastic pots in the greenhouse until they had reached the 3–4-leaf stage and then treated post-emergence in succession with the compounds according to the invention and the herbicides tested. The herbicides and the compounds of the formula I were applied in the form of aqueous suspensions or emulsions at an application rate of (converted) 300 l of water/ha. 3–4 weeks after the treatment, the plants were scored visually for any type of damage by the herbicides applied, taking into account the extent of prolonged inhibition of growth. The plants were compared with untreated controls and assessed in percentages.

Severe damage to the crop plants is markedly reduced and lesser damage is completely compensated for, even when the herbicide was greatly overdosed.

Mixtures of herbicides and compounds according to the invention are therefore outstandingly suitable for selectively controlling weeds in cereal crops.

EXAMPLE 2

The maize plants, broad-leaf weeds and grass weeds were grown in the field or in the greenhouse in plastic pots until they had reached the 3–4-leaf stage and treated post-emergence in succesion with herbicides and compounds of the formula I according to the invention. The active substances were applied in the form of aqueous suspensions or emulsions at an application rate of (converted) 300 l of water/ha. 4 weeks after the treatment, the plants were scored visually for any type of damage by the herbicides applied, taking into account in particular the extent of prolonged inhibition of growth. The plants were compared with untreated controls and assessed in percentages.

The results demonstrate that the compounds of the formula I which were employed according to the invention are capable of effectively reducing severe herbicide damage on the maize plants.

Severe damage to the crop plants is markedly reduced and lesser damage is completely compensated for, even when the herbicide was greatly overdosed.

Mixtures of herbicides and compounds according to the invention are therefore outstandingly suitable for selectively controlling weeds in maize.

The results of the biological experiments are compiled in Table 2 below.

TABLE 2

| | Crop-protective efficacy of the compounds according to the invention | | |
|---|---|---|---|
| Active substances | Dosage rate in kg of AS/ha | % Damage maize | Echinochloa millet |
| H₁ | 200 | 78 | — |
| | 100 | 75 | — |
| | 50 | 65 | — |
| | 25 | 60 | 100 |
| H₁ + S₁ | 200 + 100 | 35 | — |
| | 100 + 50 | 30 | — |

TABLE 2-continued

Crop-protective efficacy of the compounds according to the invention

| Active substances | Dosage rate in kg of AS/ha | % Damage maize | Echinochloa millet |
|---|---|---|---|
|  | 50 + 25 | 10 | — |
|  | 25 + 12 | 0 | 100 |
| H₁ + S₂ | 200 + 100 | 50 | — |
|  | 100 + 50 | 35 | — |
|  | 50 + 25 | 15 | — |
|  | 25 + 12 | 10 | 100 |
| H₁ + S₃ | 200 + 100 | 45 | — |
|  | 100 + 50 | 40 | — |
|  | 50 + 25 | 15 | — |
|  | 25 + 12 | 5 | 100 |
| H₁ + S₄ | 200 + 100 | 35 | — |
|  | 100 + 50 | 25 | — |
|  | 50 + 25 | 10 | — |
|  | 25 + 12 | 0 | 100 |

Growth stages: Maize 4-leaf stage
Echinochloa 3-leaf stage
Greenhouse experiment with 4 replications. Application using 300 liters of water/ha, scoring 4 weeks after the treatment.
S₁ (Example 34 of Table 1)
S₂ (Example 31 of Table 1)
S₃ (Example 2 of Table 1)
S₄ (Example 4 of Table 1)

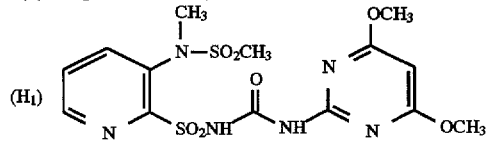
(H₁)

We claim:

1. A herbicidal composition comprising
A) at least one herbicidal active substance from the group of the sulfonylureas,
B) at least one compound of the formula I

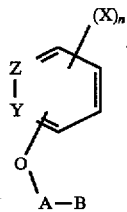

in which

Y and Z are identical or different and independently of one another are CX or N;

A is $(C_1-C_6)$-alkanediyl or $(C_3-C_8)$-alkenediyl,

B is a radical of the formula —COOR, —COSR, —CONRR⁴,

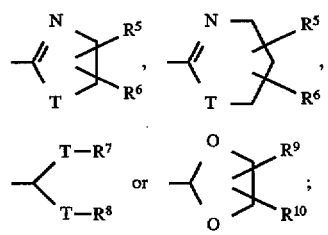

X radicals are identical or different and independently of one another are hydrogen, halogen, halo($C_1-C_8$)-alkyl, halo-($C_1-C_8$)-alkoxy, ($C_1-C_8$)-alkyl, ($C_1-C_8$)-alkoxy, nitro, amino, cyano, ($C_1-C_8$)-alkylthio or ($C_1-C_8$)-alkylsulfonyl;

n is 3;

R is hydrogen, $(C_1-C_{18})$-alkyl, $(C_3-C_{12})$-cycloalkyl, $(C_2-C_{18})$-alkenyl, $(C_2-C_8)$-alkynyl or —N=CR²R³, each of the above carbon-containing radicals optionally having one or more, preferably up to three, identical or different substituents selected from the group consisting of halogen, halo-$(C_1-C_8)$-alkoxy, nitro cyano, hydroxyl, $(C_1-C_8)$-alkoxy, in which one or more CH₂ groups can be replaced by oxygen, $(C_1-C_8)$-alkylthio, $(C_1-C_6)$-alkylsulfinyl, $(C_1-C_6)$-alkylsulfonyl, $(C_2-C_8)$-alkenylthio, $(C_2-C_8)$-alkynylthio, $(C_2-C_8)$-alkenyloxy, $(C_2-C_8)$-alkynyloxy, $(C_3-C_7)$-cycloalkyl, $(C_3-C_7)$-cycloalkoxy, mono- and di-$(C_1-C_4)$-alkylamino, $(C_1-C_8)$-alkoxycarbonyl, $(C_2-C_8)$-alkenyloxycarbonyl, $(C_2-C_8)$-alkynyloxycarbonyl, $(C_1-C_8)$-alkylthiocarbonyl, $(C_1-C_8)$-alkylcarbonyl, $(C_2-C_8)$-alkenylcarbonyl, $(C_2-C_8)$-alkynylcarbonyl, 1-(hydroxyimino)-$(C_1-C_6)$-alkyl, 1-$(C_1-C_4)$-alkylimino-$(C_1-C_6)$-alkyl, 1-$(C_1-C_4)$-alkoxyimino-$(C_1-C_6)$-alkyl, $(C_1-C_8)$-alkylcarbonylamino, $(C_2-C_8)$-alkenylcarbonylamino, $(C_2-C_8)$-alkynylcarbonylamino, carbamoyl, $(C_1-C_8)$-alkylcarbamoyl, di-$(C_1-C_6)$-alkylcarbamoyl, $(C_2-C_6)$-alkenylcarbamoyl, $(C_2-C_6)$-alkynylcarbamoyl, $(C_1-C_8)$-alkoxycarbonylamino, $(C_1-C_8)$-alkyl-aminocarbonylamino, $(C_1-C_8)$-alkoxycarbonyloxy, $(C_1-C_8)$-alkylcarbonyloxy which is unsubstituted or by halogen, nitro, $(C_1-C_4)$-alkoxy and/or optionally substituted phenyl, $(C_2-C_6)$-alkenycarbonyloxy, $(C_2-C_6)$-alkynylcarbonyloxy, phenyl, phenyl-$(C_1-C_6)$-alkoxy, phenyl-$(C_1-C_6)$-alkoxycarbonyl, phenoxy, phenoxy-$(C_1-C_6)$-alkoxy, phenoxycarbonyl, phenoxy-$(C_1-C_6)$-alkoxycarbonyl, phenylcarbonyloxy, phenylcarbonylamino, phenyl-$(C_1-C_6)$-alkylcarbonylamino, the 10 last-mentioned radicals being unsubstituted or mono- or polysubstituted, in the phenyl ring by identical or different radicals selected from the group consisting of halogen, $(C_1-C_4)$-alkyl, $(C_1-C_4)$-alkoxy, $(C_1-C_4)$-haloalkyl, $(C_1-C_4$-haloalkoxy) and nitro, —SiR²R³R⁴, —O—SiR²R³R⁴, R²R³R⁴Si—$(C_1-C_6)$-alkoxy, —CO—O—NR²R³, —O—N=CR²R³, —N=CR²R³, O—$(CH_2)_m$—CH(OR²)OR³, R'O—CHR"—CH(OR')—$(C_1-C_6)$-alkoxy and from amongst the three- to seven-membered saturated or unsaturated heterocyclic radicals which have up to three identical or different hetero atoms selected from the series consisting of S, O and N and which are optionally benzo-fused and optionally substituted by halogen and/or $(C_1-C_4)$-alkyl;

R' radicals independently of one another are $(C_1-C_4)$-alkyl, or in pairs together are a $(C_1-C_6)$-alkanediyl radical and R" is hydrogen or $(C_1-C_4)$-alkyl;

R² and R³ are identical or different and independently of one another are hydrogen, optionally substituted $(C_1-C_6)$-alkyl or optionally substituted phenyl or together are an optionally substituted $(C_2-C_6)$-alkanediyl chain;

R⁴ is hydrogen or optionally substituted $(C_1-C_4)$-alkyl; or

R and R⁴ together are alkanediyl chain which has 2 to 5 carbon atoms and in which one CH₂ group can optionally be substituted by O, NH or N($C_1-C_4$)-alkyl;

$R^5$ and $R^6$ are identical or different and independently of one another are hydrogen or $(C_1-C_6)$-alkyl;

$R^7$ and $R^8$ are identical or different and independently of one another are hydrogen or $(C_1-C_6)$-alkyl which can be substituted by halogen, $(C_1-C_4)$-alkoxy or phenyl;

$R^9$ and $R^{10}$ are identical or different and independently of one another are hydrogen or $(C_1-C_6)$-alkyl which can be substituted by halogen, $(C_1-C_4)$-alkoxy or OH;

T radicals independently of one another are oxygen or sulfur; and m is an integer from 0 to 6;

or a salt thereof, with the exception of a composition containing 2,4-dichlorophenoxyacetic acid or its alkyl ester or salt as compound of formula I.

2. A composition as claimed in claim 1, in which, in the compound of the formula I, A is $(C_1-C_4)$-alkanediyl or $(C_3-C_6)$-alkenediyl, X radicals are identical or different and independently of one another are hydrogen, halogen, halo-$(C_1-C_6)$-alkyl, halo-$(C_1-C_6)$-alkoxy, $(C_1-C_6)$-alkyl, $(C_1-C_6)$-alkoxy, nitro, amino, cyano, $(C_1-C_6)$-alkylthio or $(C_1-C_6)$-alkylsulfonyl;

where at least one radical X is hydrogen;

n is 3;

R is hydrogen, $(C_1-C_{12})$-alkyl, $(C_3-C_8)$-cycloalkyl, $(C_2-C_{12})$-alkenyl, $(C_2-C_8)$-alkynyl or $-N=CR^2R^3$, where each of the above carbon-containing radicals optionally has one or more identical or different substituents selected from the group comprising halogen, halo-$(C_1-C_8)$-alkoxy, nitro, cyano, hydroxyl, $(C_1-C_8)$-alkoxy in which one or more $CH_2$ groups can be replaced by oxygen, $(C_1-C_6)$-alkylthio, $(C_1-C_4)$-alkylsulfinyl, $(C_1-C_4)$-alkylsulfonyl, $(C_2-C_6)$-alkenylthio, $(C_2-C_6)$-alkynylthio, $(C_2-C_6)$-alkenyloxy, $(C_2-C_6)$-alkynyloxy, $(C_3-C_6)$-cycloalkyl, $(C_3-C_6)$-cycloalkoxy, mono- and di-$(C_1-C_4)$-alkylamino, $(C_1-C_6)$-alkoxycarbonyl, $(C_2-C_6)$-alkenyloxycarbonyl, $(C_2-C_6)$-alkynyloxycarbonyl, $(C_1-C_6)$-alkylthiocarbonyl, $(C_1-C_6)$-alkylcarbonyl, $(C_2-C_6)$-alkenylcarbonyl, $(C_2-C_6)$-alkynylcarbonyl, 1-(hydroxyimino)-$(C_1-C_6)$-alkyl, 1-$(C_1-C_4)$-alkylimino-$(C_1-C_4)$-alkyl, 1-$(C_1-C_4)$-alkoxyimino-$(C_1-C_4)$-alkyl, $(C_1-C_6)$-alkylcarbonylamino, $(C_2-C_6)$-alkenylcarbonylamino, $(C_2-C_6)$-alkynylcarbonylamino, carbamoyl, $(C_1-C_6)$-alkylcarbamoyl, di-$(C_1-C_4)$-alkylcarbamoyl, $(C_2-C_6)$-alkenylcarbamoyl, $(C_2-C_4)$-alkynylcarbamoyl, $(C_1-C_6)$-alkoxycarbonylamino, $(C_1-C_6)$-alkyl-amino-carbonylamino, $(C_1-C_6)$-alkoxycarbonyloxy, $(C_1-C_6)$-alkylcarbonyloxy which is unsubstituted or substituted by halogen, nitro, $(C_1-C_4)$-alkoxy and/or optionally substituted phenyl, $(C_2-C_6)$-alkenylcarbonyloxy, $(C_2-C_6)$-alkynylcarbonyloxy, phenyl, phenyl-$(C_1-C_4)$-alkoxy, phenyl-$(C_1-C_4)$-alkoxycarbonyl, phenoxy, phenoxy-$(C_1-C_4)$-alkoxy, phenoxycarbonyl, phenoxy-$(C_1-C_4)$-alkoxycarbonyl, phenylcarbonyloxy, phenylcarbonylamino, phenyl-$(C_1-C_6)$-alkylcarbonylamino, the 10 last-mentioned radicals in the phenyl ring being unsubstituted or mono- or polysubstituted by identical or different radicals selected from the group comprising halogen, $(C_1-C_4)$-alkyl, $(C_1-C_4)$-alkoxy, $(C_1-C_4)$-haloalkyl, $(C_1-C_4)$-haloalkoxy and nitro, $-SiR^2R^3R^4$, $-O-SiR^2R^3R^4$, $R^2R^3R^4Si-(C_1-C_4)$-alkoxy, $-CO-O-NR^2R^3$, $-O-N=CR^2R^3$, $-N=CR^2R^3$, $O-(CH_2)_m-CH(OR^2)OR^3$, R'O—CHR"—CH(OR')—$(C_1-C_4)$-alkoxy and from amongst the three- to seven-membered saturated or unsaturated heterocyclic radicals which have up to three identical or different hetero atoms from the series comprising S, O and N and which are optionally benzofused and optionally substituted by halogen and/or $(C_1-C_4)$-alkyl;

$R^2$ and $R^3$ are identical or different and independently of one another are hydrogen, optionally substituted $(C_1-C_4)$-alkyl or optionally substituted phenyl, or together represent an optionally substituted $(C_2-C_4)$-alkanediyl chain;

$R^5$ and $R^6$ are identical or different and independently of one another represent hydrogen or $(C_1-C_4)$-alkyl;

$R^7$ and $R^8$ are identical or different and independently of one another represent hydrogen or $(C_{-C4})$-alkyl which can be substituted by halogen, $(C_{-C4})$-alkoxy or phenyl;

$R^9$ and $R^{10}$ are identical or different and independently of one another represent hydrogen or $(C_1-C_4)$-alkyl which can be substituted by halogen, $(C_1-C_4)$-alkoxy or OH;

m is an integer from 0 to 3;

and the remaining radicals or variables are as defined in claim 1.

3. A composition as claimed in claim 1, in which, in formula I,

A is $(C_1-C_3)$-alkanediyl or $(C_1-C4_8)$-alkenediyl,

X is as defined in claim 2 and at least 2 radicals X are hydrogen;

n is 3;

R is hydrogen, $(C_1-C_{12})$-alkyl, $(C_3-C_8)$-cycloalkyl, $(C_2-C_{12})$-alkenyl, $(C_2-C_8)$-alkynyl or $-N=CR^2R^3$, where each of the above carbon-containing radicals optionally has one or more, identical or different substituents selected from the group comprising hydroxyl, $(C_1-C_8)$-alkoxy in which one or more, $CH_2$ group(s) can be replaced by oxygen, $(C_1-C_4)$-alkylthio, $(C_2-C_4)$-alkenylthio, $(C_2-C_4)$-alkynylthio, $(C_2-C_4)$-alkenyloxy, $(C_2-C_4)$-alkynyloxy, mono- and di-$(C_1-C_2)$-alkylamino, $(C_1-C_4)$-alkoxycarbonyl, $(C_2-C_4)$-alkenyloxycarbonyl, $(C_2-C_4)$-alkynyloxycarbonyl, $(C_1-C_4)$-alkylcarbonyl, $(C_2-C_4)$-alkenylcarbonyl, $(C_2-C_4)$-alkynylcarbonyl, $(C_1-C_4)$-alkylcarbonylamino, $(C_2-C_4)$-alkenylcarbonylamino, carbamoyl, $(C_1-C_8)$-alkylcarbamoyl, di-$(C_1-C_6)$-alkylcarbamoyl, $(C_1-C_4)$-alkoxycarbonyloxy, $(C_1-C_4)$-alkylcarbonyloxy which is unsubstituted or substituted by halogen and/or $(C_1-C_4)$-alkoxy, $(C_2-C_4)$-alkenylcarbonyloxy, $(C_2-C_4)$-alkynylcarbonyloxy, phenyl, phenyl-$(C_1-C_4)$-alkoxy, phenyl-$(C_1-C_4)$-alkoxycarbonyl, phenoxy, phenoxy-$(C_1-C_4)$-alkoxy, phenoxycarbonyl, phenoxy-$(C_1-C_4)$-alkoxycarbonyl, phenylcarbonyloxy, the 8 last-mentioned radicals being unsubstituted in the phenyl ring or mono- or polysubstituted identical or different radicals selected from the group comprising halogen, $(C_1-C_2)$-alkyl, $(C_1-C_2)$-alkoxy, $(C_1-C_2)$-haloalkyl, $(C_1-C_2)$-haloalkoxy and nitro, $-SiR^2R^3R^4$, $O-SiR^2R^3R^4$, $R^2R^3R^4Si-(C_1-C_4)$-alkoxy, $-O-N=CR^2R^3$, $-N=CR^2R^3$, $O-(CH_2)_m-CH(OR^2)OR^3$, R'O—CHR"—CH(OR') —$(C_1-C_4)$-alkoxy and from amongst the three- to seven-membered saturated or unsaturated heterocyclic radicals which have up to three identical or different hetero atoms selected from the series comprising S, O and N and which are optionally benzofused and optionally substituted, preferably up to trisubstituted, by halogen and/or $(C_1-C_4)$-alkyl;

R' radicals independently of one another are $(C_1-C_4)$-alkyl or in pairs together are a $(C_1-C_4)$-alkanediyl radical and R" is hydrogen or $(C_1-C_4)$-alkyl;

$R^2$ and $R^3$ are identical or different and independently of one another are hydrogen, optionally substituted $(C_1-C_4)$-alkyl or optionally substituted phenyl, or together are an optionally substituted $(C_2-C_4)$-alkanediyl chain; and $R^5$ and $R^6$ are identical or different and independently of one another are hydrogen or $(C_1-C_4)$-alkyl;

$R^7$ and $R^8$ are identical or different and independently of one another are hydrogen or $(C_1-C_4)$-alkyl which can be substituted by halogen, $(C_1-C_4)$-alkoxy or phenyl;

$R^9$ and $R^{10}$ are identical or different and independently of one another are hydrogen or $(C_1-C_4)$-alkyl which can be substituted by halogen, $(C_1-C_4)$-alkoxy or OH;

m is an integer from 0 to 2;

and the remaining radicals or variables are as defined in claim 1.

4. A method of protecting crop plants against phytotoxic secondary effects of herbicides, which comprises applying, to the plants, the seeds of the plants or the area under cultivation, an effective amount of at least one compound of the formula I which has been defined in claim 1 before, after or simultaneously with the herbicidal active substance wherein the component of the formula I and the herbicidal active substance are as defined in claim 1.

5. The method as claimed in claim 4, wherein the crop plants are cereal plants or maize plants.

6. Seed which has been dressed using at least one compound of the formula I as claimed in claim 1.

7. A herbicidal composition as claimed in claim 1, wherein

A is $(C_1-C_3)$-alkanediyl or $(C_4-C_8)$-alkenediyl, n is 3 and at least two radicals X are hydrogen.

8. A herbicidal composition as claimed in claim 7, wherein

A is $CH_2$, $CH(CH_3)$, $CH_2CH_2$, $CH_2CH_2CH_2$ or $C(CH_3)_2$.

9. A herbicidal composition as claimed in claim 8, wherein

B is a radical of the formula COOR, and

R is $(C_1-C_{12})$-alkyl which is unsubstituted or has one substituent from the group consisting of $(C_1-C_8)$-alkoxy, $(C_1-C_4)$-alkylthio, $(C_2-C_4)$-alkenyloxy, $(C_1-C_4)$-alkoxy-carbonyl, $(C_1-C_4)$-alkyl-carbonyl, $(C_1-C_4)$-alkyl-carbonyloxy which is unsubstituted or substituted by halogen, and $(C_1-C_4)$-alkylsulfonyl, or is $(C_2-C_{12})$-alkenyl.

10. A herbicidal composition as claimed in claim 9, wherein the herbicide is selected from the group consisting of phenylsulfonylurea, benzylsulfonylurea, thienylsulfonylurea and pyrazolylsulfonylurea herbicides and sulfonylureas of the sulfondiamide series, pyridylsulfonylureas and alkoxyphenoxysulfonylureas.

11. An herbicidal composition as claimed in claim 1 which comprises at least one compound of the formula I

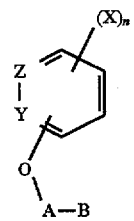

(I)

X radicals are identical or different and independently of one another are hydrogen, halogen, halo-$(C_1-C_8)$-alkyl, halo-$(C_1-C_8)$-alkoxy, $(C_1-C_8)$-alkyl, $(C_1-C_8)$-alkoxy, nitro, amino, cyano, $(C_1-C_8)$-alkylthio or $(C_1-C_8)$-alkylsulfonyl, n is 3;

$R^2$ and $R^3$ are identical or different and independently of one another are hydrogen, optionally substituted $(C_1-C_6)$-alkyl or optionally substituted phenyl, or together are an optionally substituted $(C_1-C_6)$-alkanediyl chain and A) in the event that at least one of the radicals Y and Z is nitrogen, then A is $(C_1-C_8)$-alkanediyl or $(C_3-C_6)$-alkenediyl;

B is a radical of the formula —COOR, —COSR, —CONRR$^4$,

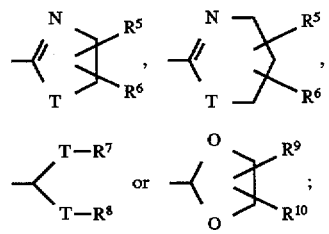

R is an equivalent of an agriculturally suitable cation, $(C_3-C_{18})$-alkyl, $(C_3-C_{12})$-cycloalkyl, $(C_3-C_{18})$-alkenyl, $(C_3-C_8)$-alkenyl or —N=$CR^2R^3$, where each of the above carbon-containing radicals optionally has one or more identical or different substituents selected from the group consisting of halogen, halo-$(C_1-C_8)$-alkoxy, nitro, cyano, hydroxyl, $(C_1-C_8)$-alkoxy in which one or more $CH_2$ groups can be replaced by oxygen, $(C_1-C_8)$-alkylthio, $(C_1-C_6)$-alkylsulfinyl, $(C_1-C_6)$-alkylsulfonyl, $(C_2-C_8)$-alkenylthio, $(C_2-C_8)$-alkynylthio, $(C_2-C_8)$-alkenyloxy, $(C_2-C_6)$-alkynyloxy, $(C_3-C_7)$-cycloalkyl, $(C_3-C_7)$-cycloalkoxy, mono- and di-$(C_1-C_4)$-alkylamino, $(C_1-C_8)$-alkoxycarbonyl, $(C_2-C_8)$-alkenyloxycarbonyl, $(C_2-C_8)$-alkynyloxycarbonyl, 1-(hydroxyimino )-$(C_1-C_6)$-alkyl, 1-$(C_1-C_4)$-alkylimino-$(C_1-C_6)$-alkyl, $(C_1-C_8)$-alkylcarbonylamino, $(C_2-C_8)$-alkenylcarbonylamino, $(C_2-C_8)$-alkynylcarbonylamino, carbamoyl, $(C_1-C_8)$-alkylcarbamoyl, di-$(C_1-C_6)$-alkylcarbamoyl, $(C_2-C_6)$-alkenylcarbamoyl, $(C_2-C_6)$-alkynylcarbamoyl, $(C_1-C_8)$-alkoxycarbonylamino, $(C_1-C_8)$-alkylaminocarbonylamino, $(C_1-C_8)$-alkoxycarbonyloxy, $(C_1-C_8)$-alkylcarbonyloxy which is unsubstituted or substituted by halogen, nitro, $(C_1-C_4)$-alkoxy and/or optionally substituted phenyl, $(C_2-C_6)$-alkenylcarbonyloxy, $(C_2-C_6)$-alkynylcarbonyloxy, phenyl, phenyl-$(C_1-C_6)$-alkoxy, phenyl-$(C_1-C_6)$-alkoxycarbonyl, phenoxy, phenoxy-$(C_1-C_6)$-alkoxy, phenoxy-$(C_1-C_6)$-alkoxycarbonyl, phenylcarbonyloxy, phenylcarbonylamino, phenyl-$(C_1-C_6)$- alkylcarbonylamino, the 9 last-mentioned radicals being unsubstituted or mono- or polysubstituted in the phenyl ring by identical or different radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and nitro, —$SiR^2R^3R^4$, —O—$SiR^2R^3R^4$, $R^2R^3R^4Si$—$(C_1-C_6)$-alkoxy, —CO—O—$NR^2R^3$, —O—N=$CR^2R^3$, —N=$CR^2R^3$ and O—$(CH_2)_m$—$CH(OR^2)OR^3$, R'O—CHR"—CH(OR')—$(C_1-C_6)$-alkoxy, and from amongst the three- to seven-membered saturated or unsaturated heterocyclic radicals which have up to three identical or different hetero atoms from the series consisting S, O and N and which are optionally benzo-fused and optionally substituted by halogen and/or $(C_1-C_4)$-alkyl;

R' radicals independently of one another are $(C_1-C_4)$-alkyl, or in pairs together are a $(C_1-C_6)$-alkanediyl radical and R" is hydrogen or $(C_1-C_4)$-alkyl, $R^4$ is hydrogen, optionally substituted $(C_1-C_4)$-alkyl or R and $R^4$ together are an alkanediyl chain which has 2 to 5 carbon atoms and in which one $CH_2$ group can optionally be replaced by O, NH or $N(C_1-C_4)$-alkyl, and $R^5$ and $R^6$ are identical or different and independently of one another are hydrogen or $(C_1-C_6)$-alkyl;

$R^7$ and $R^8$ are identical or different and independently of one another are hydrogen or $(C_1-C_6)$-alkyl which can be substituted by halogen, $(C_1-C_4)$-alkoxy or phenyl, $R^9$ and $R^{10}$ are identical or different and independently of one another are hydrogen or $(C_1-C_6)$-alkyl which can be substituted by halogen, $(C_1-C_4)$-alkoxy or OH, T radicals independently of one another are oxygen or sulfur, and m is an integer from 0 to 6;

B) or in the end that none of the radicals Y and Z is nitrogen,

A is $(C_1-C_6)$-alkanediyl or $(C_4-C_8)$-alkenediyl;

B is a radical of the formula —COOR, —COSR or —$CONRR^4$;

R is $(C_1-C_{18})$-alkyl, $(C_3-C_{12})$-cycloalkyl, $(C_2-C_{18})$-alkenyl or $(C_2-C_8)$-alkynyl where each of the above carbon-containing radicals has one or more identical or different substituents selected from the group consisting of $(C_2-C_8)$-alkylthio, $(C_2-C_8)$-alkynylthio, $(C_2-C_8)$-alkenyloxy, $(C_2-C_8)$-alkynyloxy, $(C_3-C_7)$-cycloalkyl, $(C_3-C_7)$-cycloalkoxy, $(C_7-C_{10})$-alkenyloxycarbonyl, $(C_3-C_8)$-alkynyloxycarbonyl, $(C_1-C_8)$-alkylthiocarbonyl, $(C_2-C_8)$-alkenylcarbonyl, $(C_2-C_8)$-alkynylcarbonyl, 1-(hydroxyimino)-$(C_1-C_6)$-alkyl, 1-$(C_1-C_4)$-alkylimino-$(C_1-C_6)$-alkyl, 1-$(C_1-C_4)$-alkoxyimino-$(C_1-C_6)$-alkyl, $(C_1-C_8)$-alkylcarbonylamino, $(C_2-C_8)$-alkenylcarbonylamino, $(C_2-C_8)$-alkynylcarbonylamino, carbamoyl, $(C_1-C_8)$-alkylcarbamoyl, di-$(C_1-C_6)$-alkylcarbamoyl, $(C_2-C_6)$-alkenylcarbamoyl, $(C_2-C_6)$-alkynylcarbamoyl, $(C_1-C_8)$-alkoxycarbonylamino, $(C_1-C_8)$-alkyl-amino-carbonylamino, $(C_1-C_8)$-alkoxycarbontloxy, $(C_1-C_8)$-alkylcarbonyloxy which is unsubstituted and/or substituted by halogen, nitro, $(C_1-C_4)$-alkoxy or optionally substituted phenyl, $(C_2-C_6)$-alkenylcarbonyloxy, $(C_2-C_6)$-alkynylcarbonyloxy, phenyl-$(C_2-C_6)$-alkoxy, phenyl-$(C_2-C_6)$-alkoxycarbonyl, phenoxy-$(C_1-C_6)$-alkoxy, phenoxy-$(C_2-C_6)$-alkoxycarbonyl, phenylcarbonyloxy, phenylcarbonylamino, phenyl-$(C_1-C_6)$-alkylcarbonylamino, where the 7 last-mentioned radicals are unsubstituted or mono- or polysubstituted in the phenyl ring by identical or different radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and nitro, —$SiR^2R^3R^4$, —O—$SiR^2R^3R^4$, $R^2R^3R^4Si$—$(C_1-C_6)$-alkoxy, —CO—O—$NR^2R^3$, —O—N=$CR^2R^3$, —N=$CR^2R^3$ and O—$(CH_2)_m$—CH $(OR^2)OR^3$-alkoxy and R'O—CHR"—CH(OR')—$(C_1-C_6)$-alkoxy;

R' radicals independently of one another are $(C_1-C_4)$-alkyl, or in pairs together are a $(C_1-C_6)$-alkanediyl radical and R" radicals are hydrogen or $(C_1-C_4)$-alkyl;

$R^4$ is hydrogen or optionally substituted $(C_1-C_4)$-alkyl; and m is an integer from 0 to 6.

* * * * *